United States Patent
Lecloux et al.

(10) Patent No.: US 9,496,506 B2
(45) Date of Patent: *Nov. 15, 2016

(54) DEUTERATED COMPOUNDS FOR ELECTRONIC APPLICATIONS

(71) Applicant: E I DU PONT DE NEMOURS AND COMPANY, Wilmington, DE (US)

(72) Inventors: Daniel David Lecloux, Midland, MI (US); Kalindi Dogra, Wilmington, DE (US); Weishi Wu, Landenberg, PA (US); Adam Fennimore, Wilmington, DE (US); Eric Maurice Smith, Hockessin, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 536 days.

This patent is subject to a terminal disclaimer.

(21) Appl. No.: 13/748,883

(22) Filed: Jan. 24, 2013

(65) Prior Publication Data
US 2013/0140544 A1  Jun. 6, 2013

Related U.S. Application Data

(63) Continuation of application No. 12/643,515, filed on Dec. 21, 2009, now abandoned.

(51) Int. Cl.
| | |
|---|---|
| *H01L 51/00* | (2006.01) |
| *H01L 51/05* | (2006.01) |
| *H01L 51/50* | (2006.01) |
| *C09K 11/06* | (2006.01) |
| *C07D 487/04* | (2006.01) |

(52) U.S. Cl.
CPC ......... *H01L 51/0072* (2013.01); *C07D 487/04* (2013.01); *C09K 11/06* (2013.01); *H01L 51/0067* (2013.01); *H01L 51/0508* (2013.01); *H01L 51/0034* (2013.01); *H01L 51/0085* (2013.01); *H01L 51/5016* (2013.01); *H01L 2251/308* (2013.01)

(58) Field of Classification Search
CPC .......... C07D 487/04; H01L 2251/308; H01L 51/0034; H01L 51/0067; H01L 51/0072; H01L 51/0085; H01L 51/0508; H01L 51/5016; C09K 11/06
See application file for complete search history.

(56) References Cited

U.S. PATENT DOCUMENTS

| | | | |
|---|---|---|---|
| 3,282,875 | A | 11/1966 | Connolly et al. |
| 3,849,458 | A | 11/1974 | Dinh-Nguyen |
| 4,053,311 | A | 10/1977 | Limburg et al. |

(Continued)

FOREIGN PATENT DOCUMENTS

| | | |
|---|---|---|
| CN | 1668719 A | 9/2005 |
| CN | 1711334 A | 12/2005 |

(Continued)

OTHER PUBLICATIONS

"Color" (Definition) Web. Sep. 27, 2011, <http://hyperphysicsphy-astr.gsu/Hbase/vision/secpl>.

(Continued)

*Primary Examiner* — Dawn Garrett

(57) ABSTRACT

This invention relates to deuterated indolocarbazole compounds that are useful in electronic applications. It also relates to electronic devices in which the active layer includes such a deuterated compound.

13 Claims, 3 Drawing Sheets

(56) References Cited

U.S. PATENT DOCUMENTS

| | | |
|---|---|---|
| 4,358,545 A | 11/1982 | Ezzell et al. |
| 4,940,525 A | 7/1990 | Ezzell |
| 5,247,190 A | 9/1993 | Friend et al. |
| 5,254,633 A | 10/1993 | Han |
| 5,378,519 A | 1/1995 | Kikuchi et al. |
| 5,408,109 A | 4/1995 | Heeger et al. |
| 5,707,747 A | 1/1998 | Tomiyama et al. |
| 5,911,918 A | 6/1999 | Shacklette et al. |
| 5,929,194 A | 7/1999 | Woo et al. |
| 5,936,259 A | 8/1999 | Katz et al. |
| 5,942,340 A | 8/1999 | Hu et al. |
| 5,962,631 A | 10/1999 | Woo et al. |
| 6,150,426 A | 11/2000 | Howard et al. |
| 6,259,202 B1 | 7/2001 | Sturm et al. |
| 6,303,238 B1 | 10/2001 | Thompson et al. |
| 6,579,630 B2 | 6/2003 | Li et al. |
| 6,670,645 B2 | 12/2003 | Grushin et al. |
| 6,677,060 B2 | 1/2004 | Li et al. |
| 6,686,067 B2 | 2/2004 | Li et al. |
| 6,852,429 B1 | 2/2005 | Li et al. |
| 6,872,475 B2 | 3/2005 | Chen et al. |
| 6,875,524 B2 | 4/2005 | Hatwar et al. |
| 6,902,833 B2 | 6/2005 | Thompson et al. |
| 6,953,705 B2 | 10/2005 | Prakash |
| 7,023,013 B2 | 4/2006 | Ricks et al. |
| 7,075,102 B2 | 7/2006 | Grushin et al. |
| 7,125,952 B2 | 10/2006 | O'Dell et al. |
| 7,173,131 B2 | 2/2007 | Saitoh et al. |
| 7,189,989 B2 | 3/2007 | Ise |
| 7,211,202 B2 | 5/2007 | Korzhenko et al. |
| 7,235,420 B2 | 6/2007 | Prakash et al. |
| 7,351,358 B2 | 4/2008 | Hsu et al. |
| 7,358,409 B2 | 4/2008 | Saitoh et al. |
| 7,362,796 B2 | 4/2008 | Shigeno |
| 7,365,230 B2 | 4/2008 | Herron et al. |
| 7,375,250 B2 | 5/2008 | Saitoh et al. |
| 7,390,438 B2 | 6/2008 | Hsu et al. |
| 7,402,681 B2 | 7/2008 | Ong et al. |
| 7,431,866 B2 | 10/2008 | Hsu et al. |
| 7,456,424 B2 | 11/2008 | Wu et al. |
| 7,462,298 B2 | 12/2008 | Hsu et al. |
| 7,491,450 B2 | 2/2009 | Okinaka et al. |
| 7,528,542 B2 | 5/2009 | Kawamura et al. |
| 7,540,978 B2 | 6/2009 | Pfeiffer et al. |
| 7,586,006 B2 | 9/2009 | Funahashi |
| 7,642,380 B2 | 1/2010 | Funahashi |
| 7,651,786 B2 | 1/2010 | Matsuura et al. |
| 7,651,788 B2 | 1/2010 | Seo et al. |
| 7,709,104 B2 | 5/2010 | Saitoh et al. |
| 7,722,785 B2 | 5/2010 | Hsu et al. |
| 7,745,017 B2 | 6/2010 | Nakamura et al. |
| 7,887,933 B2 | 2/2011 | Kathirgamanathan et al. |
| 8,026,665 B2 | 9/2011 | Kim et al. |
| 8,062,769 B2 | 11/2011 | Kai et al. |
| 8,063,399 B2 | 11/2011 | Johansson et al. |
| 8,217,181 B2 | 7/2012 | Wang |
| 8,343,381 B1 | 1/2013 | Chesterfield |
| 8,431,245 B2* | 4/2013 | Meng ............... C09K 11/06 257/40 |
| 8,617,720 B2* | 12/2013 | Howard, Jr. ......... C09K 11/06 257/40 |
| 9,293,716 B2* | 3/2016 | Feldman ............ C09K 11/06 |
| 2001/0026878 A1 | 10/2001 | Woo et al. |
| 2001/0053462 A1 | 12/2001 | Mishima |
| 2002/0048687 A1 | 4/2002 | Hosokawa et al. |
| 2002/0076576 A1 | 6/2002 | Li et al. |
| 2002/0155319 A1 | 10/2002 | Kawamura et al. |
| 2003/0072966 A1 | 4/2003 | Hosokawa et al. |
| 2003/0118866 A1 | 6/2003 | Oh et al. |
| 2003/0134140 A1 | 7/2003 | Li et al. |
| 2003/0138657 A1 | 7/2003 | Li et al. |
| 2003/0168970 A1 | 9/2003 | Tominaga et al. |
| 2003/0224205 A1 | 12/2003 | Li et al. |
| 2003/0227001 A1 | 12/2003 | Li et al. |
| 2004/0004433 A1 | 1/2004 | Lamansky et al. |
| 2004/0038459 A1 | 2/2004 | Brown et al. |
| 2004/0068132 A1* | 4/2004 | Lecloux ............... C07F 9/5077 556/18 |
| 2004/0082250 A1 | 4/2004 | Haoto |
| 2004/0094768 A1 | 5/2004 | Yu et al. |
| 2004/0102577 A1 | 5/2004 | Hsu et al. |
| 2004/0106003 A1 | 6/2004 | Chen et al. |
| 2004/0106004 A1 | 6/2004 | Li |
| 2004/0121184 A1 | 6/2004 | Thompson et al. |
| 2004/0127637 A1 | 7/2004 | Hsu et al. |
| 2004/0209118 A1 | 10/2004 | Seo et al. |
| 2004/0263067 A1 | 12/2004 | Saitoh et al. |
| 2005/0031898 A1 | 2/2005 | Li et al. |
| 2005/0035335 A1 | 2/2005 | Han et al. |
| 2005/0063638 A1 | 3/2005 | Alger et al. |
| 2005/0064233 A1 | 3/2005 | Matsuura et al. |
| 2005/0073249 A1 | 4/2005 | Morii et al. |
| 2005/0088083 A1 | 4/2005 | Seo |
| 2005/0158577 A1 | 7/2005 | Ishibashi et al. |
| 2005/0184287 A1 | 8/2005 | Herron et al. |
| 2005/0186106 A1 | 8/2005 | Li et al. |
| 2005/0187411 A1 | 8/2005 | Herron et al. |
| 2005/0191776 A1 | 9/2005 | Lamansky et al. |
| 2005/0205860 A1 | 9/2005 | Hsu et al. |
| 2005/0244670 A1 | 11/2005 | Saitoh et al. |
| 2005/0245752 A1 | 11/2005 | Conley et al. |
| 2005/0280008 A1 | 12/2005 | Ricks et al. |
| 2006/0033421 A1 | 2/2006 | Matsuura et al. |
| 2006/0043858 A1 | 3/2006 | Ikeda et al. |
| 2006/0052641 A1 | 3/2006 | Funahashi |
| 2006/0076557 A1 | 4/2006 | Waller et al. |
| 2006/0103298 A1 | 5/2006 | Lee |
| 2006/0113528 A1 | 6/2006 | Okinaka et al. |
| 2006/0115678 A1 | 6/2006 | Saitoh et al. |
| 2006/0121312 A1 | 6/2006 | Yamada et al. |
| 2006/0127698 A1 | 6/2006 | Tokailin et al. |
| 2006/0128969 A1 | 6/2006 | Li et al. |
| 2006/0134459 A1 | 6/2006 | Huo |
| 2006/0152146 A1 | 7/2006 | Funahashi |
| 2006/0154107 A1 | 7/2006 | Kubota et al. |
| 2006/0158102 A1 | 7/2006 | Kawamura et al. |
| 2006/0159838 A1 | 7/2006 | Kowalski et al. |
| 2006/0194074 A1 | 8/2006 | Funahashi |
| 2006/0210830 A1 | 9/2006 | Funahashi |
| 2006/0216411 A1 | 9/2006 | Steudel et al. |
| 2006/0217572 A1 | 9/2006 | Kawamura et al. |
| 2006/0251925 A1 | 11/2006 | Hosokawa et al. |
| 2006/0267488 A1 | 11/2006 | Saitoh et al. |
| 2006/0284140 A1 | 12/2006 | Breuning et al. |
| 2007/0031588 A1 | 2/2007 | Nakayama |
| 2007/0031701 A1 | 2/2007 | Nakashima et al. |
| 2007/0032632 A1 | 2/2007 | Tsukioka et al. |
| 2007/0063638 A1 | 3/2007 | Tokairin et al. |
| 2007/0066755 A1 | 3/2007 | Hsu et al. |
| 2007/0079927 A1 | 4/2007 | Lamansky et al. |
| 2007/0087222 A1 | 4/2007 | Kim et al. |
| 2007/0096082 A1 | 5/2007 | Gaynor et al. |
| 2007/0114917 A1 | 5/2007 | Funahashi et al. |
| 2007/0134511 A1 | 6/2007 | Kawamura et al. |
| 2007/0155991 A1 | 7/2007 | Funahashi |
| 2007/0181874 A1 | 8/2007 | Prakash et al. |
| 2007/0189190 A1 | 8/2007 | Feng et al. |
| 2007/0205409 A1 | 9/2007 | Lecloux et al. |
| 2007/0215864 A1 | 9/2007 | Luebben et al. |
| 2007/0228364 A1 | 10/2007 | Radu et al. |
| 2007/0236137 A1 | 10/2007 | Funahashi |
| 2007/0247063 A1 | 10/2007 | Murase et al. |
| 2007/0252511 A1 | 11/2007 | Funahashi |
| 2007/0255076 A1 | 11/2007 | Ito et al. |
| 2007/0285009 A1 | 12/2007 | Kubota |
| 2007/0292713 A9 | 12/2007 | Dobbs et al. |
| 2007/0298530 A1 | 12/2007 | Feehery |
| 2008/0023676 A1 | 1/2008 | Hsu |
| 2008/0049413 A1 | 2/2008 | Jinde et al. |
| 2008/0067473 A1 | 3/2008 | Walker et al. |
| 2008/0071049 A1 | 3/2008 | Radu et al. |
| 2008/0086012 A1 | 4/2008 | Egawa et al. |
| 2008/0097076 A1 | 4/2008 | Radu et al. |
| 2008/0102312 A1 | 5/2008 | Parham et al. |

(56) References Cited

U.S. PATENT DOCUMENTS

| | | | |
|---|---|---|---|
| 2008/0114178 A1 | 5/2008 | Kawakami et al. | |
| 2008/0138655 A1 | 6/2008 | Lecloux et al. | |
| 2008/0166566 A1 | 7/2008 | Prakash | |
| 2008/0191614 A1 | 8/2008 | Kim et al. | |
| 2008/0233433 A1 | 9/2008 | Igarashi et al. | |
| 2008/0286566 A1 | 11/2008 | Prakash | |
| 2008/0286605 A1 | 11/2008 | Takeda | |
| 2008/0297037 A1 | 12/2008 | Vestweber et al. | |
| 2008/0303425 A1 | 12/2008 | Rostovtsev et al. | |
| 2008/0303427 A1 | 12/2008 | Johansson et al. | |
| 2008/0303428 A1 | 12/2008 | Rostovtsev et al. | |
| 2008/0315754 A1 | 12/2008 | Kawamura et al. | |
| 2009/0051281 A1 | 2/2009 | Inoue | |
| 2009/0058279 A1 | 3/2009 | Takeda | |
| 2009/0079334 A1 | 3/2009 | Kim et al. | |
| 2009/0114909 A1 | 5/2009 | Li et al. | |
| 2009/0134781 A1 | 5/2009 | Jang et al. | |
| 2009/0184635 A1 | 7/2009 | Pan et al. | |
| 2009/0206748 A1 | 8/2009 | Moriwaki et al. | |
| 2009/0295274 A1 | 12/2009 | Hwang et al. | |
| 2009/0302742 A1 | 12/2009 | Komori et al. | |
| 2010/0108989 A1 | 5/2010 | Busing et al. | |
| 2010/0148161 A1 | 6/2010 | Kai et al. | |
| 2010/0148162 A1 | 6/2010 | Komori et al. | |
| 2010/0187505 A1 | 7/2010 | Stoessel et al. | |
| 2010/0187506 A1 | 7/2010 | Park et al. | |
| 2010/0187977 A1 | 7/2010 | Kai et al. | |
| 2010/0187983 A1 | 7/2010 | Herron et al. | |
| 2010/0213825 A1 | 8/2010 | Park et al. | |
| 2010/0314644 A1 | 12/2010 | Nishimura et al. | |
| 2011/0037062 A1 | 2/2011 | Fukumatsu et al. | |
| 2011/0095269 A1 | 4/2011 | Zhang et al. | |
| 2011/0095273 A1 | 4/2011 | Meng et al. | |
| 2011/0121269 A1 | 5/2011 | Lecloux et al. | |
| 2011/0147718 A1 | 6/2011 | Howard et al. | |
| 2013/0264561 A1* | 10/2013 | Dobbs | C09K 11/06 257/40 |

FOREIGN PATENT DOCUMENTS

| | | | |
|---|---|---|---|
| CN | 1768029 A | 5/2006 | |
| CN | 1957646 A | 5/2007 | |
| DE | 102005058557 A1 | 6/2007 | |
| EP | 443861 B1 | 5/1995 | |
| EP | 681019 A2 | 9/1999 | |
| EP | 1061112 A1 | 12/2000 | |
| EP | 765106 A2 | 11/2002 | |
| EP | 1277824 A1 | 1/2003 | |
| EP | 1317005 A2 | 6/2003 | |
| EP | 1437395 A2 | 7/2004 | |
| EP | 1491609 A2 | 12/2004 | |
| EP | 1491610 A2 | 12/2004 | |
| EP | 1541657 A1 | 6/2005 | |
| EP | 1561794 A1 | 8/2005 | |
| EP | 1604974 A1 | 12/2005 | |
| EP | 1612202 A1 | 1/2006 | |
| EP | 1624500 A1 | 2/2006 | |
| EP | 1672713 A1 | 6/2006 | |
| EP | 1718124 A1 | 11/2006 | |
| EP | 1737277 A1 | 12/2006 | |
| EP | 1792893 A1 | 6/2007 | |
| EP | 1860096 A1 | 11/2007 | |
| EP | 1932895 A1 | 6/2008 | |
| EP | 1933603 A1 | 6/2008 | |
| EP | 1956022 A1 | 8/2008 | |
| EP | 1995292 A1 | 11/2008 | |
| EP | 2080762 A1 | 7/2009 | |
| EP | 2085450 A1 | 8/2009 | |
| EP | 2093271 A1 | 8/2009 | |
| EP | 2067766 A1 | 10/2009 | |
| EP | 2067767 A1 | 10/2009 | |
| EP | 2189508 A2 | 5/2010 | |
| JP | 04175395 A | 6/1992 | |
| JP | 07/249490 A | 9/1995 | |
| JP | 08/053397 A | 2/1996 | |
| JP | 08/167479 A | 6/1996 | |
| JP | 10251633 A | 9/1998 | |
| JP | 2000/186066 A | 7/2000 | |
| JP | 2001/226331 A | 8/2001 | |
| JP | 2003/238501 A | 8/2003 | |
| JP | 2003/297582 A | 10/2003 | |
| JP | 2003/338380 A | 11/2003 | |
| JP | 2004-10550 | 1/2004 | |
| JP | 2004/071286 A | 3/2004 | |
| JP | 2005/232452 A | 9/2005 | |
| JP | 2006/016384 A | 1/2006 | |
| JP | 2006/052323 A | 2/2006 | |
| JP | 2006-151844 A | 6/2006 | |
| JP | 2006/176493 A | 7/2006 | |
| JP | 2006-219392 A | 8/2006 | |
| JP | 2007-182432 A | 7/2007 | |
| JP | 2007-186449 A | 7/2007 | |
| JP | 2009-161470 A | 7/2009 | |
| JP | 2009-246354 A | 10/2009 | |
| KR | 10-2004-0079803 A | 9/2004 | |
| KR | 10-2009-0046731 A | 5/2009 | |
| KR | 10-2009-0086920 A | 8/2009 | |
| KR | 10-2009-0093897 A | 9/2009 | |
| KR | 10-2009-0086015 A | 10/2009 | |
| WO | 00/53565 A1 | 9/2000 | |
| WO | 00/70655 A2 | 11/2000 | |
| WO | 01/41512 A1 | 6/2001 | |
| WO | 03/008424 A1 | 1/2003 | |
| WO | 03/040257 A1 | 5/2003 | |
| WO | 03/063555 A1 | 7/2003 | |
| WO | 03/091688 A2 | 11/2003 | |
| WO | 2004/016710 A1 | 2/2004 | |
| WO | 2004/018587 A1 | 3/2004 | |
| WO | 2005/000787 A1 | 1/2005 | |
| WO | 2005/031889 A2 | 4/2005 | |
| WO | 2005/049546 A1 | 6/2005 | |
| WO | 2005/052027 A1 | 6/2005 | |
| WO | 2006/025273 A1 | 3/2006 | |
| WO | 2006/043087 A1 | 4/2006 | |
| WO | 2006/063852 A1 | 6/2006 | |
| WO | 2006/112582 A1 | 10/2006 | |
| WO | 2006/121237 A1 | 11/2006 | |
| WO | 2007/021117 A1 | 2/2007 | |
| WO | 2007/065678 A1 | 6/2007 | |
| WO | 2007/100096 A1 | 9/2007 | |
| WO | 2007/105917 A1 | 9/2007 | |
| WO | 2007/108666 A1 | 9/2007 | |
| WO | 2008/011953 A1 | 1/2008 | |
| WO | 2008/024378 A2 | 2/2008 | |
| WO | 2008/024379 A2 | 2/2008 | |
| WO | WO 2008/056746 | * 5/2008 | |
| WO | 2008/147721 A1 | 12/2008 | |
| WO | 2008/149968 A1 | 12/2008 | |
| WO | 2009/018009 A1 | 2/2009 | |
| WO | 2009/028902 A2 | 3/2009 | |
| WO | 2009/055628 A1 | 4/2009 | |
| WO | 2009/067419 A1 | 5/2009 | |
| WO | 2009/069790 A1 | 6/2009 | |
| WO | 2009/136596 A1 | 11/2009 | |
| WO | 2010/065494 A2 | 6/2010 | |
| WO | 2010/071362 A2 | 6/2010 | |
| WO | 2010/075421 A2 | 7/2010 | |
| WO | 2010/098246 A1 | 9/2010 | |
| WO | 2010/099534 A2 | 9/2010 | |
| WO | 2010/135403 A2 | 11/2010 | |
| WO | 2011/053334 A1 | 5/2011 | |

OTHER PUBLICATIONS

Appleby et al, Polymeric Perfluoro Bis-Sulfanomides As Possible Fuel Cell Electrolytes, J. Electrochem Soc. 1993, vol. 140, pp. 109-111.

Borello et al, "Photodetectors", Kirk-Othmer Encyclopedia of Chemical Technology, 4$^{th}$ Edition, 1999, vol. 18, pp. 1537-1538.

Braun, et al, "Visible Light Emission From Semiconducting Polymer Diodes", Applied Physics Letters, 1991, vol. 58, (18), pp. 1982-1984.

(56) References Cited

OTHER PUBLICATIONS

Gustafsson, "Flexible Light-Emitting Diodes Made From Soluble Conducting Polymer", Nature, vol. 357, pp. 477-479 (Jun. 11, 1992).
Kirk-Othmer Encyclopedia of Chemical Technology, Fourth Edition, vol. 18, p. 837-860, 1996 by Y. Wang.
CRC Handbook of Chemistry and Physics, 81$^{st}$ Ed., (2000-2001) (Book Not Included).
Markus, John, Electronics and Nucleonics Dictionary, 470 and 476 (Mcgraw-Hill 1966).
Chen et al, "Efficient Blue Light-Emitting Diodes Using Cross-Linked Layers of Polymeric Arylamine and Fluorene", Synthetic Metals, 1999, vol. 107, pp. 129-138.
Chu et al, "Highly Efficient and Stable Inverted Bottom-Emission Organic Light-Emitting Devices", Applied Physics Letters, 2006, vol. 89, pp. 053503-1 to 053503-3.
Beckmann et al, "Methyl Reorientation in Solid 3-Ethychrysene and 3-Isopropylesene; Solid State Nuclear Magnetic Resonance" 1998; vol. 12, pp. 251-256.
Carey et al., Structure and Mechanisms; Advanced Organic Chemistry, Part A, 5$^{th}$ Ed., pp. 142-145.
Chu et al., "Comparitive Study of Single and Multiemissive Layers in Inverted White Organic Light-Emitting Devices", Applied Physics Letters, 2006, vol. 89, No. 11, p. 113502.
Danel et al., "Blue-Emitting Anthracenes With End-Capping Diarylamines", Chem. Mater., 2002, vol. 14, pp. 3860-3865.
Eaton et al, "Dihedral Angle of Biphenyl in Solution and the Molecular Force Field", J. Chem. Soc. Faraday Trans. 2, 1973, 60 pp. 1601-1608.
Hartwig, "Carbon-Heteroatom Bond Formation Catalyzed by Organometallic Complexes", Nature, 2008, vol. 455, No. 18, pp. 314-322.
Hartwig, "Discovery and Understanding of Transition-Metal-Catalyzed Aromatic Subbstitution Reactions", Syn. Letters, 2006, No. 9, pp. 1283-1294.
Ishiyama et al, "Palladium(0)-Catalyzed Cross-Couplin Reaction of Alkoxydiboron with Haloarenes: A Direct Procedure for Arylboronic Esters", Journal of Organic Chemistry, 1995, vol. 60, pp. 7508-7510.
Kim et al, "Synthesis and Electroluminescent Properties of Highly Efficient Anthracene Derivatives With Bulky Side Groups", Organic Electronics, 2009, vol. 10, No. 5, pp. 822-833.
Klaerner et al, "Cross-Linkable Polymers Based on Dialkylfluorenes", Chemistry of Materials, 1999, 11, pp. 1800-1805.
Kodomari et al, "Selective Halogenation of Aromatic Hydrocarbons", Journal of Organic Chemistry, 1988, vol. 53, p. 2093.
Kumada, "Nickel and Palladium Complex Catalyzed Cross-Coupling Reactions of Organometallic Reagents With Organic Halides", Pure & Applied Chemistry, 1980, vol. 52, pp. 669-679.
Leznoff et al, "Photocyclization of Aryl Polyenes. V. Photochemical Synthesis of Substituted Chrysenes", Canadian Journal of Chemistry, 1972, vol. 50, pp. 528-533.
Mueller et al, "Synthesis and Characterization of Soluble Oligo(9, 10-Anthrylene)S," Chemische Berichte, 1994, 127, pp. 437-444.
Murata et al, "Novel Palladium(0)-Catalyzed Coupling Reaction of Dialkoxyborane With Aryl Halides: A Convenient Synthetic Route to Arylboronates", Journal of Organic Chemistry, 1997, vol. 62, pp. 6458-6459.
Colon et al, "High Molecular Weight Aromatic Polymers by Nickel Coupling of Aryl Polychlorides", Journal of Polymer Science, Part A, Polymer Chemistry Edition, 1990, vol. 28, pp. 367-383.
Constantini et al, "Infrared Spectroscopic Study of Polaron Formation in Electrochemically Synthesized Poly(3-Alkylpyrroles), "Phys. Chem. Chem. Phys., 2003, vol. 5, pp. 749-757.
Desmarteau, "Novel Perfluorinated Ionomers and Ionenes", Journal of Fluorine Chemistry, 1995, vol. 72, pp. 203-208.
Feiring et al, "Aromatic Monomers With Pendant Fluoroalkylsulfonate and Sulfonimide Groups", Journal of Fluorine Chemistry, 2000, vol. 105, pp. 129-135.
Feiring et al, "Novel Aromatic Polymers With Pendant Lithium Perfluoroalkylsulfonate or Sulfinimide Groups", Macromolecules, 2000, vol. 33, pp. 9262-9271.
He et al, "A Hole-Transporting Material With Contollable Morphology Containing Binaphthyl and Triphenylamine Chromophores", Advanced Functional Materials, 2006, vol. 16, No. 10, pp. 1343-1348.
He et al, "High-Efficiency Organic Polymer Light-Emitting Heterostructure Devices on Flexible Plastic Substrates", Applied Physics Letters, 2000, vol. 76, No. 6, pp. 661-663.
Lee et al, "A Thermally Stable Hole Injection Material for Use in Organic Light-Emitting Diodes", Thin Solid Films, 2007, vol. 515, pp. 7726-7731.
Lee et al, "Poly(Thieno(3,4-B)Thiophene) A New Stable Low Band Gap Conducting Polymer", Macromolecules, 2001, vol. 34, pp. 5746-5747.
Maeda et al, "Alkynylpyrenes As Improved Pyrene-Based Biomolecular Probes With the Advantages of High Fluorescence Quantum Yields and Long Absorption/Emission Wavelengths", Chemistry—A European Journal, 2006, vol. 12(3), pp. 824-831.
March, "Aromatization of Six-Membered Rings", Advanced Organic Chemistry, Wiley-Interscience (1992), 4$^{th}$ Ed., pp. 1162-1164.
Minabe et al, "Electrophilic Substitution of Monosubstituted Pyrenes", Bulletin of the Chemical Society of Japan, 1994, vol. 67(1), pp. 172-179.
Noji et al, "A New Catalytic System for Aerobic Oxidative Coupling of 2-Naphthol Derivatives by the Use of Cucl-Amine Complex: A Practical Synthesis of Binaphthol Derivatives", Tetrahedron Letters, 1994, vol. 35, No. 43, pp. 7983-7984.
Norman, et al, "The Reactions of Pyrene With Free Radicals and With Sodium", Journal of the Chemical Society, 1958, pp. 175-179.
Park et al, "Ab Inition Study of Pyrenes for Blue Organic Light-Emitting Diodes", Molecular Crystals and Liquid Crystals, 2006, vol. 444, pp. 177-184.
Murata et al, "Palladium-Catalyzed Borylation of Aryl Halides or Triflates With Dialkoxyborane: A Novel and Facile Synthetic Route to Aryboronates", Journal of Organic Chemistry, 2000, vol. 65, No. 1, pp. 164-168.
Negishi et al, III.2.15 Palladium Catalyzed Conjugate Substitution; Handbook of Organopalladium Chemistry for Organic Synthesis, 2000, vol. 1, pp. 767-789.
Negishi, "Palladium-Or Nickel-Catalyzed Cross Coupling, A New Selective Method for Carbon-Carbon Bond Formation", Accounts of Chemical Research, 1982, vol. 15, pp. 340-348.
Stille, "The Palladium-Catalyzed Cross-Coupling Reactions of Organotin Reagents With Organic Electrophiles", Angew. Chem. Int. Ed. Engl., 1986, vol. 25, pp. 508-524.
Tong et al, "Enhancement of Oled Efficiencies and High-Voltage Stabilities of Light-Emitting Materials by Deuterzation", Journal of Physical Chemistry, 2007, vol. 111, pp. 3490-3494.
Wang et al, "Novel Bis(8-Hydroxyquinoline)Phenolate-Aluminum Complexes for Organic Light-Emitting Diodes", Synthetic Metals, 2002, vol. 131, 1-3, pp. 1-5.
Weine et al, "Reactions of an O-Quinone Monoimide With Anthracenes, Phencyclone, and 1,3-Diphenylisobenzofuran", Journal of Organic Chemistry, 1989, vol. 54, pp. 5926-5930.
Wellmann et al, "Highi-Efficiency P-I-N Organic Light-Emitting Diodes With Long Lifetime", Journal of the SID, 2005, vol. 13/5, pp. 393-397.
Yamada et al, Synthesis of 2,9-Dichloro-1, 10-Phenanthroline From N,N'-Annelated Phenanthrolinediones, Bulletin of the Chemical Society of Japan, 1990, vol. 63, No. 9, pp. 2710-2712.
Yamamoto et al, "Electrically Conducting and Thermally Stable-Conjugated Poly(Arylene)S Prepared by Organometallic Process", Progress in Polymer Science, 1992, vol. 17, pp. 1153-1205.
Yan et al, "Synthesis and Nonlinear Optical Properties of Novel Multi-Branched Two-Photon Polymerization Initiators", Journal of Material Chemistry, 2004, vol. 14, pp. 2295-3000.

(56) References Cited

OTHER PUBLICATIONS

Zhu et al, "An Improved Preparation of Arylboronates: Application in One-Pot Suzuki Biaryl Synthesis", Journal of Organic Chemistry, 2003, vol. 68, pp. 3729-3732.

Zhu et al, "Effect of Ito Carrier Concentration on the Performance of Lighti-Emitting Diodes", 2000; Material Research Society; Chem Abstract 134: 122994.

Zhao et al, "Solid-State Dye-Sensitized Photovoltaic Device With Newly Designed Small Organic Molecule As Hole-Conductor", Chemical Physical Letters, 2007, vol. 445, pp. 259-264.

Tokito et al, "Highly Efficient Blue-Green Emission From Organic Light-Emitting Diodes Using Dibenzochrysene Derivatives", Applied Physics Letters, vol. 77, No. 2, pp. 160-162, date: 2000.

* cited by examiner

DEUTERATED COMPOUNDS FOR ELECTRONIC APPLICATIONS

RELATED APPLICATION DATA

This application claims priority under 35 U.S.C. §119(e) from U.S. Provisional Application No. 61/256,012 filed on Oct. 29, 2009, which is incorporated by reference herein in its entirety.

BACKGROUND

1. Field of the Disclosure

This invention relates to indolocarbazole derivative compounds which are at least partially deuterated. It also relates to electronic devices in which at least one active layer includes such a compound.

2. Description of the Related Art

Organic electronic devices that emit light, such as light-emitting diodes that make up displays, are present in many different kinds of electronic equipment. In all such devices, an organic active layer is sandwiched between two electrical contact layers. At least one of the electrical contact layers is light-transmitting so that light can pass through the electrical contact layer. The organic active layer emits light through the light-transmitting electrical contact layer upon application of electricity across the electrical contact layers.

It is well known to use organic electroluminescent compounds as the active component in light-emitting diodes. Simple organic molecules such as anthracene, thiadiazole derivatives, and coumarin derivatives are known to show electroluminescence. Semiconductive conjugated polymers have also been used as electroluminescent components, as has been disclosed in, for example, U.S. Pat. No. 5,247,190, U.S. Pat. No. 5,408,109, and Published European Patent Application 443 861. In many cases the electroluminescent compound is present as a dopant in a host material.

There is a continuing need for new materials for electronic devices.

SUMMARY

There is provided an indolocarbazole derivative having at least one deuterium substituent.

There is also provided an electronic device comprising an active layer comprising the above compound.

There is further provided an electroactive composition comprising (a) an indolocarbazole derivative having at least one deuterium substituent and (b) an electroactive dopant capable of electroluminescence having an emission maximum between 380 and 750 nm.

BRIEF DESCRIPTION OF THE DRAWINGS

Embodiments are illustrated in the accompanying figures to improve understanding of concepts as presented herein.

Figure 1A:
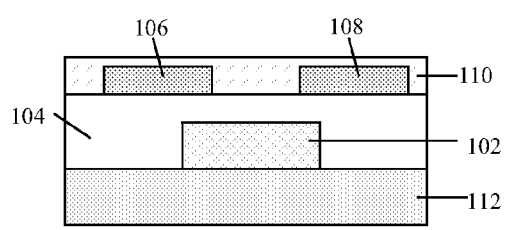
FIG. 1A includes a schematic diagram of an organic field effect transistor (OTFT) showing the relative positions of the active layers of such a device in bottom contact mode.

Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION

Many aspects and embodiments are disclosed herein and are exemplary and not limiting. After reading this specification, skilled artisans appreciate that other aspects and embodiments are possible without departing from the scope of the invention.

Other features and benefits of any one or more of the embodiments will be apparent from the following detailed description, and from the claims. The detailed description first addresses Definitions and Clarification of Terms followed by the Deuterated Compound, the Electronic Device, and finally Examples.

1. Definitions and Clarification of Terms

Before addressing details of embodiments described below, some terms are defined or clarified.

As used herein, the term "aliphatic ring" is intended to mean a cyclic group that does not have delocalized pi electrons. In some embodiments, the aliphatic ring has no unsaturation. In some embodiments, the ring has one double or triple bond.

The term "alkoxy" refers to the group RO—, where R is an alkyl.

The term "alkyl" is intended to mean a group derived from an aliphatic hydrocarbon having one point of attachment, and includes a linear, a branched, or a cyclic group. The term is intended to include heteroalkyls. The term "hydrocarbon alkyl" refers to an alkyl group having no heteroatoms. The term "deuterated alkyl" is a hydrocarbon alkyl having at least one available H replaced by D. In some embodiments, an alkyl group has from 1-20 carbon atoms.

The term "branched alkyl" refers to an alkyl group having at least one secondary or tertiary carbon. The term "secondary alkyl" refers to a branched alkyl group having a secondary carbon atom. The term "tertiary alkyl" refers to a branched alkyl group having a tertiary carbon atom. In some embodiments, the branched alkyl group is attached via a secondary or tertiary carbon.

The term "aryl" is intended to mean a group derived from an aromatic hydrocarbon having one point of attachment. The term "aromatic compound" is intended to mean an organic compound comprising at least one unsaturated cyclic group having delocalized pi electrons. The term is intended include heteroaryls. The term "hydrocarbon aryl" is intended to mean aromatic compounds having no heteroatoms in the ring. The term aryl includes groups which have a single ring and those which have multiple rings which can be joined by a single bond or fused together. The term "deuterated aryl" refers to an aryl group having at least one available H bonded directly to the aryl replaced by D. The term "arylene" is intended to mean a group derived from an aromatic hydrocarbon having two points of attachment. In some embodiments, an aryl group has from 3-60 carbon atoms.

The term "aryloxy" refers to the group RO—, where R is an aryl.

The term "compound" is intended to mean an electrically uncharged substance made up of molecules that further consist of atoms, wherein the atoms cannot be separated by physical means. The phrase "adjacent to," when used to refer to layers in a device, does not necessarily mean that one layer is immediately next to another layer. On the other hand, the phrase "adjacent R groups," is used to refer to R groups that are next to each other in a chemical formula (i.e., R groups that are on atoms joined by a bond).

The term "deuterated" is intended to mean that at least one H has been replaced by D. The deuterium is present in at least 100 times the natural abundance level. A "deuterated derivative" of compound X has the same structure as compound X, but with at least one D replacing an H.

The term "dopant" is intended to mean a material, within a layer including a host material, that changes the electronic characteristic(s) or the targeted wavelength(s) of radiation emission, reception, or filtering of the layer compared to the electronic characteristic(s) or the wavelength(s) of radiation emission, reception, or filtering of the layer in the absence of such material.

The term "electroactive" when referring to a layer or material, is intended to mean a layer or material that exhibits electronic or electro-radiative properties. In an electronic device, an electroactive material electronically facilitates the operation of the device. Examples of electroactive materials include, but are not limited to, materials which conduct, inject, transport, or block a charge, where the charge can be either an electron or a hole, and materials which emit radiation or exhibit a change in concentration of electron-hole pairs when receiving radiation. Examples of inactive materials include, but are not limited to, planarization materials, insulating materials, and environmental barrier materials.

The prefix "hetero" indicates that one or more carbon atoms have been replaced with a different atom. In some embodiments, the different atom is N, O, or S.

The term "host material" is intended to mean a material to which a dopant is added. The host material may or may not have electronic characteristic(s) or the ability to emit, receive, or filter radiation. In some embodiments, the host material is present in higher concentration.

The term "indolocarbazole" refers to the moiety

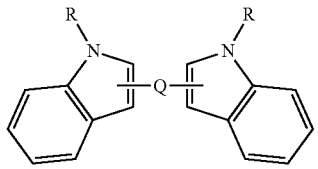

where Q represents a phenyl ring to which the nitrogen-containing rings are fused in any orientation, and R represents H or a substituent.

The term "layer" is used interchangeably with the term "film" and refers to a coating covering a desired area. The term is not limited by size. The area can be as large as an entire device or as small as a specific functional area such as the actual visual display, or as small as a single sub-pixel.

Layers and films can be formed by any conventional deposition technique, including vapor deposition, liquid deposition (continuous and discontinuous techniques), and thermal transfer. Continuous deposition techniques, include but are not limited to, spin coating, gravure coating, curtain coating, dip coating, slot-die coating, spray coating, and continuous nozzle coating. Discontinuous deposition techniques include, but are not limited to, ink jet printing, gravure printing, and screen printing.

The term "organic electronic device" or sometimes just "electronic device" is intended to mean a device including one or more organic semiconductor layers or materials. All groups can be substituted or unsubstituted unless otherwise indicated. In some embodiments, the substituents are selected from the group consisting of D, halide, alkyl, alkoxy, aryl, aryloxy, cyano, and $NR_2$, where R is alkyl or aryl.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The IUPAC numbering system is used throughout, where the groups from the Periodic Table are numbered from left to right as 1-18 (CRC Handbook of Chemistry and Physics, $81^{st}$ Edition, 2000).

2. Deuterated Compound

The new deuterated compound is an indolocarbazole derivative compound having at least one D. In some embodiments, the compound is at least 10% deuterated. By this is meant that at least 10% of the H are replaced by D. In some embodiments, the compound is at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated. In some embodiments, the compounds are 100% deuterated.

In one embodiment, the deuterated compound has Formula I or Formula II:

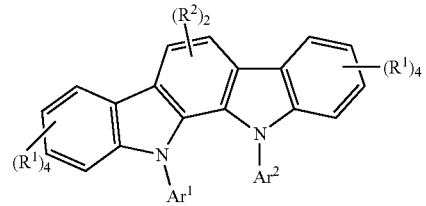

Formula I

Formula II

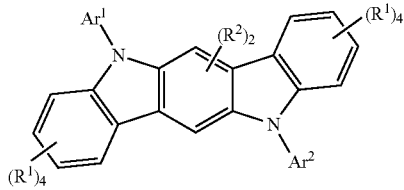

wherein:

Ar¹ is an aromatic electron transporting group;

Ar² is selected from the group consisting of aryl groups and aromatic electron transporting groups; and R¹ and R² are the same or different at each occurrence and are selected from the group consisting of H, D and aryl;

wherein the compound has at least one D.

In some embodiments of Formula I and Formula II, deuterium is present on a moiety selected from the group consisting of the indolocarbazole core, an aryl ring, a substituent group on an aryl ring, and combinations thereof.

In some embodiments, the indolocarbazole core is at least 10% deuterated. In this case, at least one of R¹ and R² is D. In some embodiments, the indolocarbazole core is at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated; in some embodiments, 100% deuterated.

Ar¹ is an aromatic electron transporting group. In some embodiments, the aromatic electron transporting group is a nitrogen-containing heteroaromatic group. Some examples of nitrogen-containing heteroaromatic groups which are electron transporting include, but are not limited to those shown below.

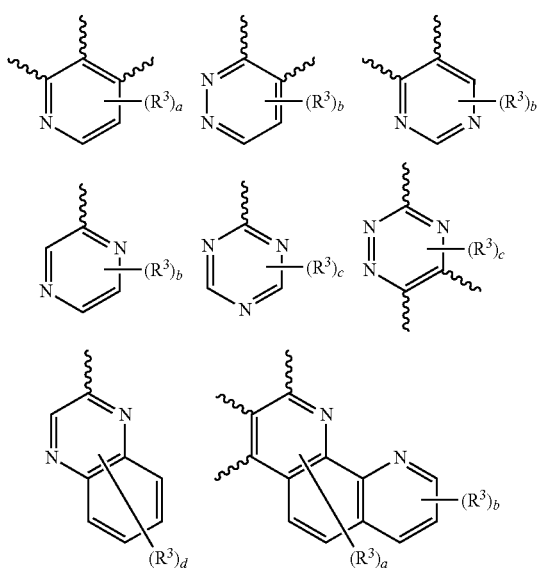

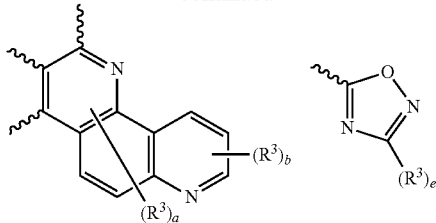

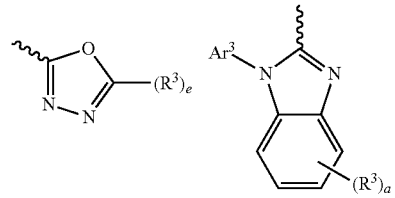

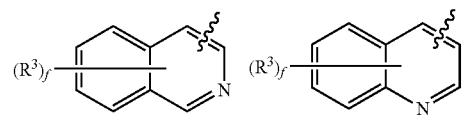

In the above formulae:

Ar³ is an aryl group;

R³ is the same or different at each occurrence and is selected from the group consisting of D, alkyl, alkoxy, aryl, aryloxy, siloxane, and silyl;

a is an integer from 0-4;

b is an integer from 0-3;

c is an integer from 0-2;

d is an integer from 0-5;

e is 0 or 1; and f is an integer from 0-6.

The group can be bonded to the nitrogen on the core at any of the positions indicated with the wavy line.

In some embodiments, two or more of the same or different electron-withdrawing substituents are bonded together to form oligomeric substituents. In some embodiments, R³ is selected from the group consisting of D and aryl. In some embodiments, R³ is a nitrogen-containing heteroaromatic electron transporting group.

In some embodiments, Ar¹ is at least 10% deuterated; in some embodiments, at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated; in some embodiments, 100% deuterated.

In some embodiments, Ar² is an aromatic electron transporting group as discussed above. In some embodiments, Ar² is selected from the group consisting of phenyl, naphthyl, phenanthryl, anthracenyl, phenylnaphthylene, naphthylphenylene, deuterated derivatives thereof, and a group having Formula III:

Formula III

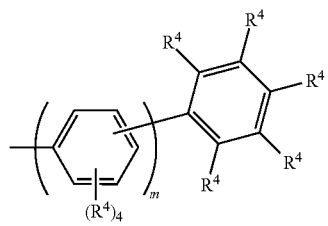

where:
R[4] is the same or different at each occurrence and is selected from the group consisting of H, D, alkyl, alkoxy, siloxane and silyl, or adjacent R[4] groups may be joined together to form an aromatic ring; and m is the same or different at each occurrence and is an integer from 1 to 6.

In some embodiments, $Ar^2$ is at least 10% deuterated; in some embodiments, at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated; in some embodiments, 100% deuterated.

In some embodiments, $R^1$ and $R^2$ are aryl. In some embodiments, the aryl group is selected from the group consisting of phenyl, naphthyl, phenanthryl, anthracenyl, phenylnaphthylene, naphthylphenylene, deuterated derivatives thereof, and a group having Formula III, shown above. In some embodiments, the aryl group has one or more substituents selected from the group consisting of D, alkyl, alkoxy, aryl, aryloxy, siloxane, silyl, deuterated derivatives thereof, and combinations thereof.

In some embodiments, $R^1$ and $R^2$ are H or D.

Some non-limiting examples of compounds having Formula I or Formula II include Compounds H1 through H14 below:

Compound H1

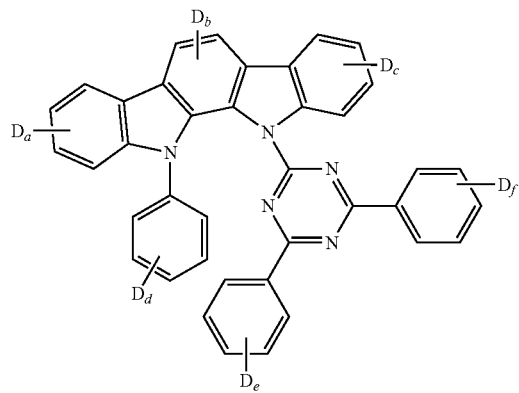

Σ(a-f) = 1-25

Compound H2

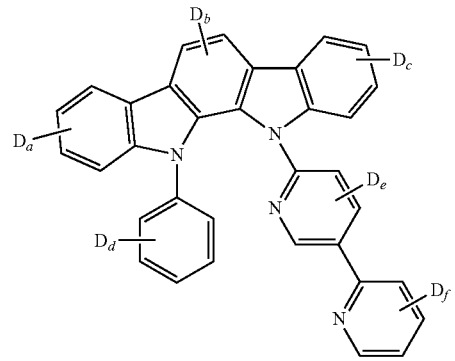

Σ(a-f) = 1-24

Compound H3

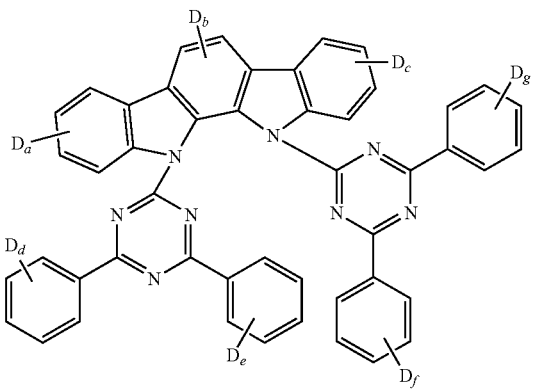

Σ(a-g) = 1-30

Compound H4

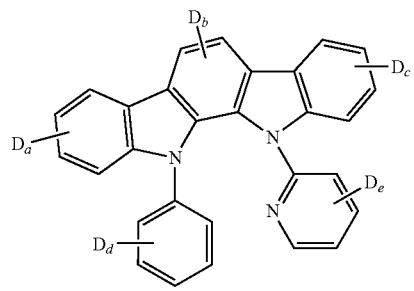

Σ(a-e) = 1-19

Compound H5

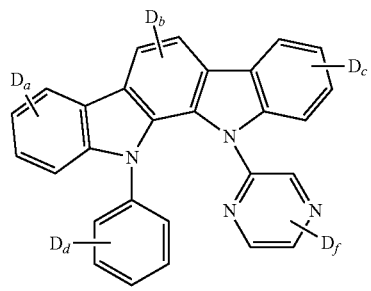

Σ(a-f) = 1-18

Compound H6
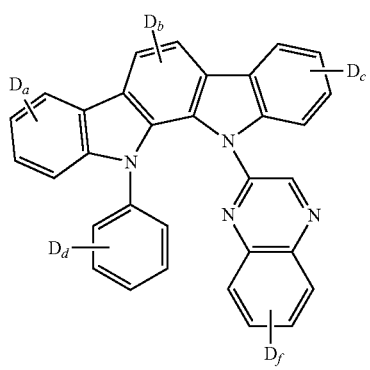
Σ(a-f) = 1-20
Compound H7
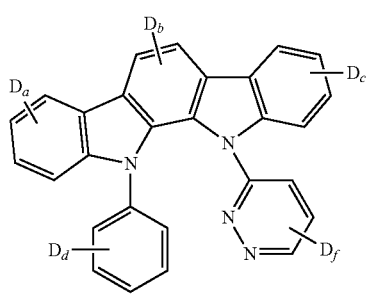
Σ(a-f) = 1-18
Compound H8
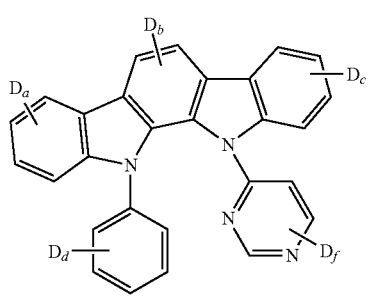
Σ(a-f) = 1-18
Compound H9
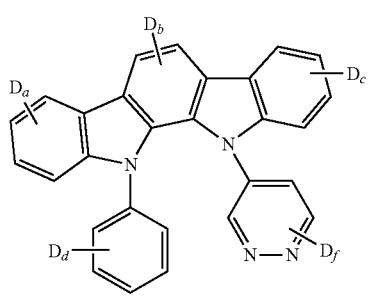
Σ(a-f) = 1-18
Compound H10
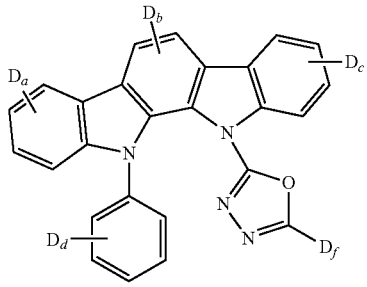
Σ(a-f) = 1-16
Compound H11
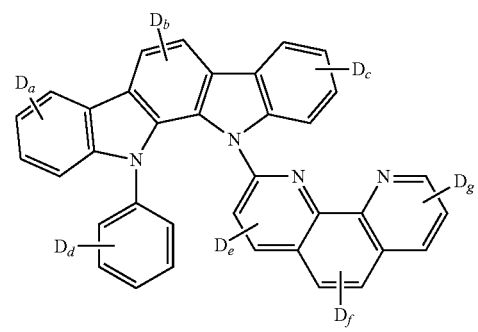
Σ(a-g) = 1-23
Compound H12
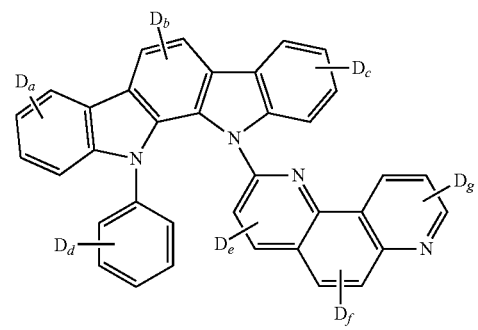
Σ(a-g) = 1-23
Compound H13
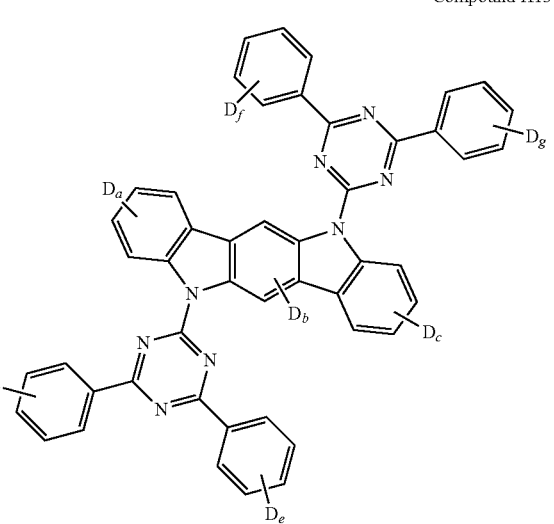
Σ(a-g) = 1-30

Compound H14
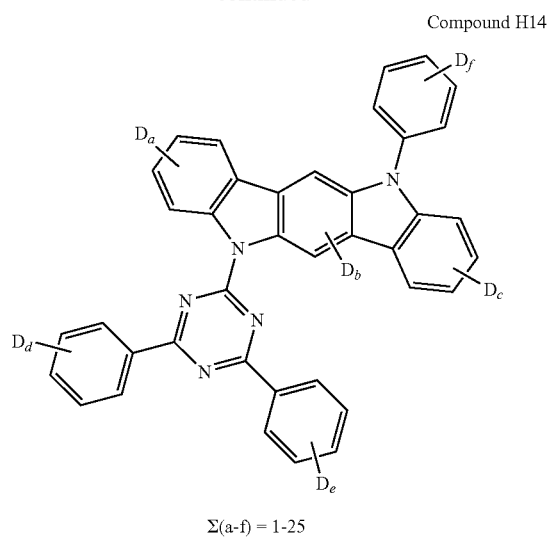
Σ(a-f) = 1-25
Compound H15
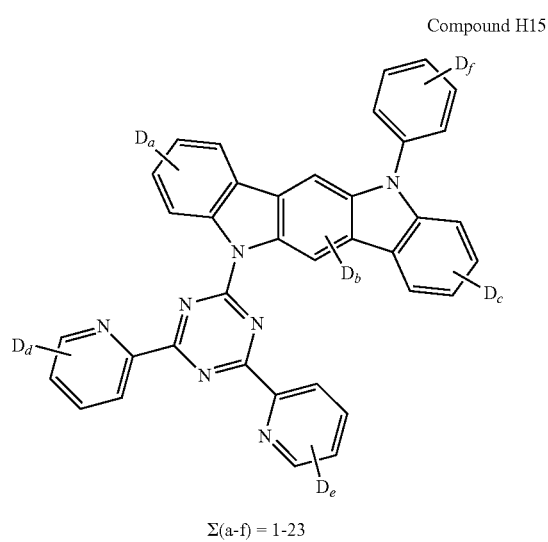
Σ(a-f) = 1-23
Compound H16
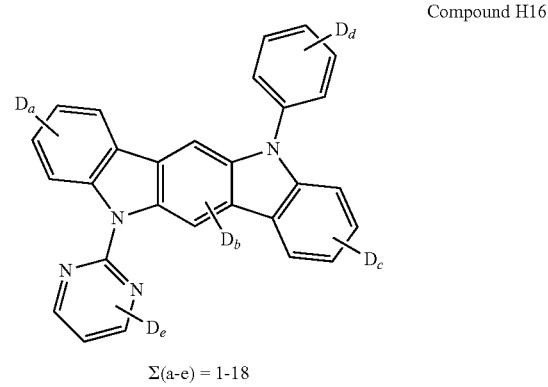
Σ(a-e) = 1-18
Compound H17
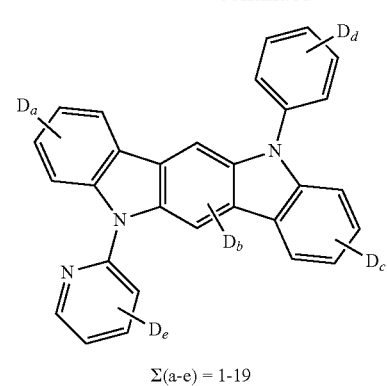
Σ(a-e) = 1-19
Compound H18
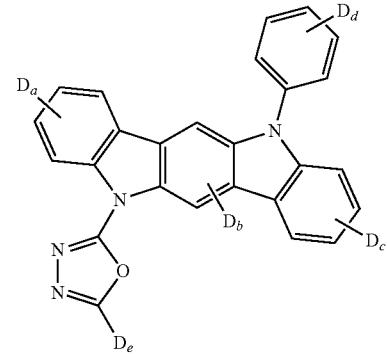
Σ(a-e) = 1-16
Compound H19
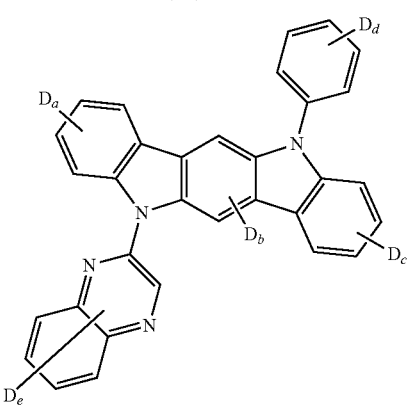
Σ(a-e) = 1-20
Compound H20
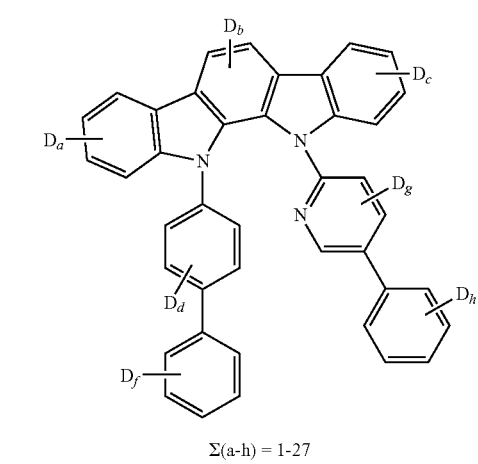
Σ(a-h) = 1-27

-continued

Compound H21

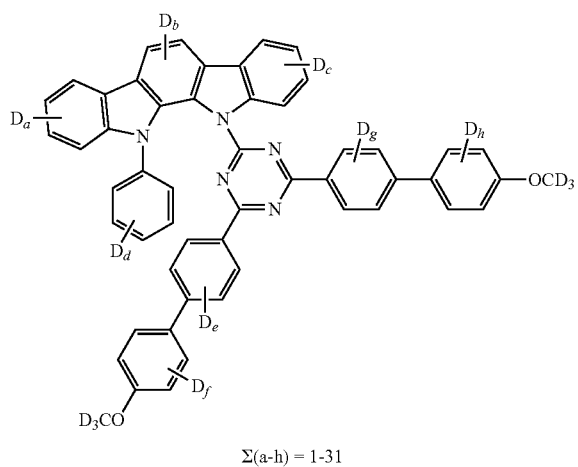

Σ(a-h) = 1-31

The non-deuterated analogs of the new compounds can be prepared by known coupling and substitution reactions. Such reactions are well-known and have been described extensively in the literature. Exemplary references include: Yamamoto, Progress in Polymer Science, Vol. 17, p 1153 (1992); Colon et al., Journal of Polymer Science, Part A, Polymer chemistry Edition, Vol. 28, p. 367 (1990); U.S. Pat. No. 5,962,631, and published PCT application WO 00/53565; T. Ishiyama et al., *J. Org. Chem.* 1995 60, 7508-7510; M. Murata et al., *J. Org. Chem.* 1997 62, 6458-6459; M. Murata et al., *J. Org. Chem.* 2000 65, 164-168; L. Zhu, et al., *J. Org. Chem.* 2003 68, 3729-3732; Stille, J. K. *Angew. Chem. Int. Ed. Engl.* 1986, 25, 508; Kumada, M. *Pure. Appl. Chem.* 1980, 52, 669; Negishi, E. *Acc. Chem. Res.* 1982, 15, 340.

The new deuterated compound can be prepared in a similar manner using deuterated precursor materials or, more generally, by treating the non-deuterated compound with deuterated solvent, such as d6-benzene, in the presence of a Lewis acid H/D exchange catalyst, such as aluminum trichloride or ethyl aluminum chloride, or acids such as $CF_3COOD$, DCl, etc. Exemplary preparations are given in the Examples. The level of deuteration can be determined by NMR analysis and by mass spectrometry, such as Atmospheric Solids Analysis Probe Mass Spectrometry (ASAP-MS). The starting materials of the perdeuterated or partially deuterated aromatic compounds or alky compounds can be purchased from the commercial source or can be obtained using known methods. Some examples of such methods can be found in a) "Efficient H/D Exchange Reactions of Alkyl-Substituted Benzene Derivatives by Means of the Pd/C—H2-D2O System" Hiroyoshi Esaki, Fumiyo Aoki, Miho Umemura, Masatsugu Kato, Tomohiro Maegawa, Yasunari Monguchi, and Hironao Sajiki Chem. Eur. J. 2007, 13, 4052-4063. b) "Aromatic H/D Exchange Reaction Catalyzed by Groups 5 and 6 Metal Chlorides" GUO, Qiao-Xia, SHEN, Bao-Jian; GUO, Hai-Qing TAKAHASHI, Tamotsu *Chinese Journal of Chemistry*, 2005, 23, 341-344; c) "A novel deuterium effect on dual charge-transfer and ligand-field emission of the cis-dichlorobis(2,2'-bipyridine)iridium (III) ion" Richard J. Watts, Shlomo Efrima, and Horia Metiu *J. Am. Chem. Soc.*, 1979, 101 (10), 2742-2743; d) "Efficient H-D Exchange of Aromatic Compounds in Near-Critical D20 Catalysed by a Polymer-Supported Sulphonic Acid" Carmen Boix and Martyn Poliakoff Tetrahedron Letters 40 (1999) 4433-4436; e) U.S. Pat. No. 3,849,458; f) "Efficient C—H/C-D Exchange Reaction on the Alkyl Side Chain of Aromatic Compounds Using Heterogeneous Pd/C in D2O" Hironao Sajiki, Fumiyo Aoki, Hiroyoshi Esaki, Tomohiro Maegawa, and Kosaku Hirota *Org. Lett.*, 2004, 6 (9), 1485-1487.

The compounds described herein can be formed into films using liquid deposition techniques. Surprisingly and unexpectedly, these compounds have greatly improved properties when compared to analogous non-deuterated compounds. Electronic devices including an active layer with the compounds described herein, have greatly improved lifetimes. In addition, the lifetime increases are achieved without deleteriously affecting other device properties. Furthermore, the deuterated compounds described herein have greater air tolerance than the non-deuterated analogs. This can result in greater processing tolerance both for the preparation and purification of the materials and in the formation of electronic devices using the materials.

3. Organic Electronic Device

Organic electronic devices that may benefit from having one or more layers comprising the deuterated materials described herein include, but are not limited to, (1) devices that convert electrical energy into radiation (e.g., a light-emitting diode, light-emitting diode display, light-emitting luminaire, or diode laser), (2) devices that detect signals through electronics processes (e.g., photodetectors, photoconductive cells, photoresistors, photoswitches, phototransistors, phototubes, IR detectors), (3) devices that convert radiation into electrical energy, (e.g., a photovoltaic device or solar cell), and (4) devices that include one or more electronic components that include one or more organic semi-conductor layers (e.g., a thin film transistor or diode). The compounds of the invention often can be useful in applications such as oxygen sensitive indicators and as luminescent indicators in bioassays.

In one embodiment, an organic electronic device comprises at least one layer comprising an indolocarbazole derivative having at least one deuterium substituent. In some embodiments, the indolocarbazole derivative has Formula I or Formula II as discussed above.

a. First Exemplary Device

A particularly useful type of transistor, the thin-film transistor (TFT), generally includes a gate electrode, a gate dielectric on the gate electrode, a source electrode and a drain electrode adjacent to the gate dielectric, and a semi-conductor layer adjacent to the gate dielectric and adjacent to the source and drain electrodes (see, for example, S. M. Sze, Physics of Semiconductor Devices, $2^{nd}$ edition, John Wiley and Sons, page 492). These components can be assembled in a variety of configurations. An organic thin-film transistor (OTFT) is characterized by having an organic semiconductor layer.

In one embodiment, an OTFT comprises:
a substrate
an insulating layer;
a gate electrode;
a source electrode;
a drain electrode; and
an organic semiconductor layer comprising an indolocarbazole compound having at least one deuterium substituent;
wherein the insulating layer, the gate electrode, the semiconductor layer, the source electrode and the drain electrode can be arranged in any sequence provided that the gate electrode and the semiconductor layer both contact the insulating layer, the source electrode and the drain electrode both contact the semiconductor layer and the electrodes are not in contact with each other. In some embodiments, the indolocarbazole derivative has Formula I or Formula II.

In FIG. 1A, there is schematically illustrated an organic field effect transistor (OTFT) showing the relative positions of the active layers of such a device in "bottom contact mode." (In "bottom contact mode" of an OTFT, the drain and source electrodes are deposited onto the gate dielectric layer prior to depositing the active organic semiconductor layer onto the source and drain electrodes and any remaining exposed gate dielectric layer.) A substrate 112 is in contact with a gate electrode 102 and an insulating layer 104 on top of which the source electrode 106 and drain electrode 108 are deposited. Over and between the source and drain electrodes are an organic semiconductor layer 110 comprising a compound of Formula 2.

Figure 1B:
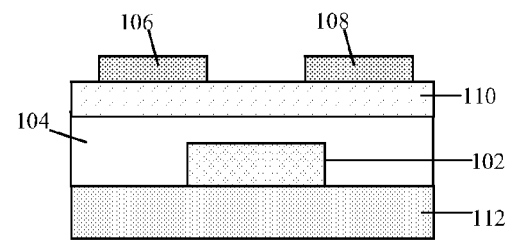
FIG. 1B includes a schematic diagram of an OTFT showing the relative positions of the active layers of such a device in top contact mode.

FIG. 1B is a schematic diagram of an OTFT showing the relative positions of the active layers of such a device in top contact mode. (In "top contact mode," the drain and source electrodes of an OTFT are deposited on top of the active organic semiconductor layer.)

Figure 1C:
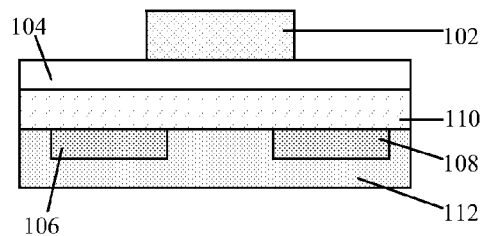
FIG. 1C includes a schematic diagram of an organic field effect transistor (OTFT) showing the relative positions of the active layers of such a device in bottom contact mode with the gate at the top.

FIG. 1C is a schematic diagram of OTFT showing the relative positions of the active layers of such a device in bottom contact mode with the gate at the top.

Figure 1D:
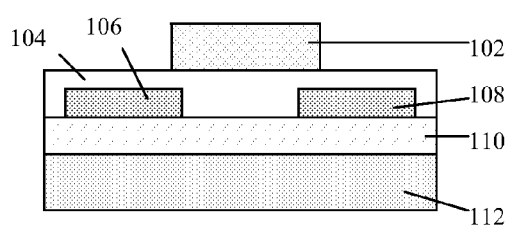
FIG. 1D includes a schematic diagram of an organic field effect transistor (OTFT) showing the relative positions of the active layers of such a device in bottom contact mode with the gate at the top.

FIG. 1D is a schematic diagram of an OTFT showing the relative positions of the active layers of such a device in top contact mode with the gate at the top.

The substrate can comprise inorganic glasses, ceramic foils, polymeric materials (for example, acrylics, epoxies, polyamides, polycarbonates, polyimides, polyketones, poly(oxy-1,4-phenyleneoxy-1,4-phenylenecarbonyl-1,4-phenylene) (sometimes referred to as poly(ether ether ketone) or PEEK), polynorbornenes, polyphenyleneoxides, poly(ethylene naphthalenedicarboxylate) (PEN), poly(ethylene terephthalate) (PET), poly(phenylene sulfide) (PPS)), filled polymeric materials (for example, fiber-reinforced plastics (FRP)), and/or coated metallic foils. The thickness of the substrate can be from about 10 micrometers to over 10 millimeters; for example, from about 50 to about 100 micrometers for a flexible plastic substrate; and from about 1 to about 10 millimeters for a rigid substrate such as glass or silicon. Typically, a substrate supports the OTFT during manufacturing, testing, and/or use. Optionally, the substrate can provide an electrical function such as bus line connection to the source, drain, and electrodes and the circuits for the OTFT.

The gate electrode can be a thin metal film, a conducting polymer film, a conducting film made from conducting ink or paste or the substrate itself, for example heavily doped silicon. Examples of suitable gate electrode materials include aluminum, gold, chromium, indium tin oxide, conducting polymers such as polystyrene sulfonate-doped poly (3,4-ethylenedioxythiophene) (PSS-PEDOT), conducting ink/paste comprised of carbon black/graphite or colloidal silver dispersion in polymer binders. In some OTFTs, the same material can provide the gate electrode function and also provide the support function of the substrate. For example, doped silicon can function as the gate electrode and support the OTFT.

The gate electrode can be prepared by vacuum evaporation, sputtering of metals or conductive metal oxides, coating from conducting polymer solutions or conducting inks by spin coating, casting or printing. The thickness of the gate electrode can be, for example, from about 10 to about 200 nanometers for metal films and from about 1 to about 10 micrometers for polymer conductors.

The source and drain electrodes can be fabricated from materials that provide a low resistance ohmic contact to the semiconductor layer, such that the resistance of the contact between the semiconductor layer and the source and drain electrodes is less than the resistance of the semiconductor layer. Channel resistance is the conductivity of the semiconductor layer. Typically, the resistance should be less than the channel resistance. Typical materials suitable for use as source and drain electrodes include aluminum, barium, calcium, chromium, gold, silver, nickel, palladium, platinum, titanium, and alloys thereof; carbon nanotubes; conducting polymers such as polyaniline and poly(3,4-ethylenedioxythiophene)/poly-(styrene sulfonate) (PEDOT:PSS); dispersions of carbon nanotubes in conducting polymers; dispersions of a metal in a conducting polymer; and multilayers thereof. Some of these materials are appropriate for use with n-type semiconductor materials and others are appropriate for use with p-type semiconductor materials, as is known to those skilled in the art. Typical thicknesses of source and drain electrodes are about, for example, from about 40 nanometers to about 1 micrometer. In some embodiments, the thickness is about 100 to about 400 nanometers.

The insulating layer comprises an inorganic material film or an organic polymer film. Illustrative examples of inorganic materials suitable as the insulating layer include aluminum oxides, silicon oxides, tantalum oxides, titanium oxides, silicon nitrides, barium titanate, barium strontium titanate, barium zirconate titanate, zinc selenide, and zinc sulfide. In addition, alloys, combinations, and multilayers of the aforesaid materials can be used for the insulating layer. Illustrative examples of organic polymers for the insulating layer include polyesters, polycarbonates, poly(vinyl phenol), polyimides, polystyrene, poly(methacrylate)s, poly (acrylate)s, epoxy resins and blends and multilayers thereof. The thickness of the insulating layer is, for example from about 10 nanometers to about 500 nanometers, depending on the dielectric constant of the dielectric material used. For example, the thickness of the insulating layer can be from about 100 nanometers to about 500 nanometers. The insulating layer can have a conductivity that is, for example, less than about $10^{-12}$ S/cm (where S=Siemens=1/ohm).

The insulating layer, the gate electrode, the semiconductor layer, the source electrode, and the drain electrode are formed in any sequence as long as the gate electrode and the semiconductor layer both contact the insulating layer, and the source electrode and the drain electrode both contact the semiconductor layer. The phrase "in any sequence" includes sequential and simultaneous formation. For example, the source electrode and the drain electrode can be formed simultaneously or sequentially. The gate electrode, the source electrode, and the drain electrode can be provided using known methods such as physical vapor deposition (for example, thermal evaporation or sputtering) or ink jet printing. The patterning of the electrodes can be accomplished by known methods such as shadow masking, additive photolithography, subtractive photolithography, printing, microcontact printing, and pattern coating.

For the bottom contact mode OTFT (FIG. 1A), electrodes 106 and 108, which form channels for source and drain respectively, can be created on the silicon dioxide layer using a photolithographic process. A semiconductor layer 110 is then deposited over the surface of electrodes 106 and 108 and layer 104.

In one embodiment, semiconductor layer 110 comprises one or more compounds represented by Formula 2. The semiconductor layer 110 can be deposited by various techniques known in the art. These techniques include thermal evaporation, chemical vapor deposition, thermal transfer, ink-jet printing and screen-printing. Dispersion thin film coating techniques for deposition include spin coating, doctor blade coating, drop casting and other known techniques.

For top contact mode OTFT (FIG. 1B), layer 110 is deposited on layer 104 before the fabrication of electrodes 106 and 108.

b. Second Exemplary Device

The present invention also relates to an electronic device comprising at least one active layer positioned between two electrical contact layers, wherein the at least one active layer of the device includes an indolocarbazole compound having at least one deuterium substitutent.

Figure 2:
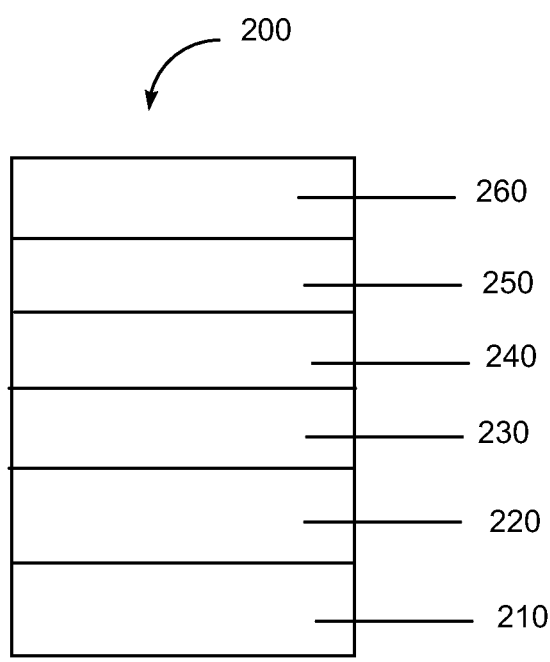
FIG. 2 includes a schematic diagram of another example of an organic electronic device.

Another example of an organic electronic device structure is shown in FIG. 2. The device 200 has a first electrical contact layer, an anode layer 210 and a second electrical contact layer, a cathode layer 260, and an electroactive layer 240 between them. Adjacent to the anode may be a hole injection layer 220. Adjacent to the hole injection layer may be a hole transport layer 230, comprising hole transport material. Adjacent to the cathode may be an electron transport layer 250, comprising an electron transport material. Devices may use one or more additional hole injection or hole transport layers (not shown) next to the anode 210 and/or one or more additional electron injection or electron transport layers (not shown) next to the cathode 260.

Layers 220 through 250 are individually and collectively referred to as the active layers.

Figure 3:
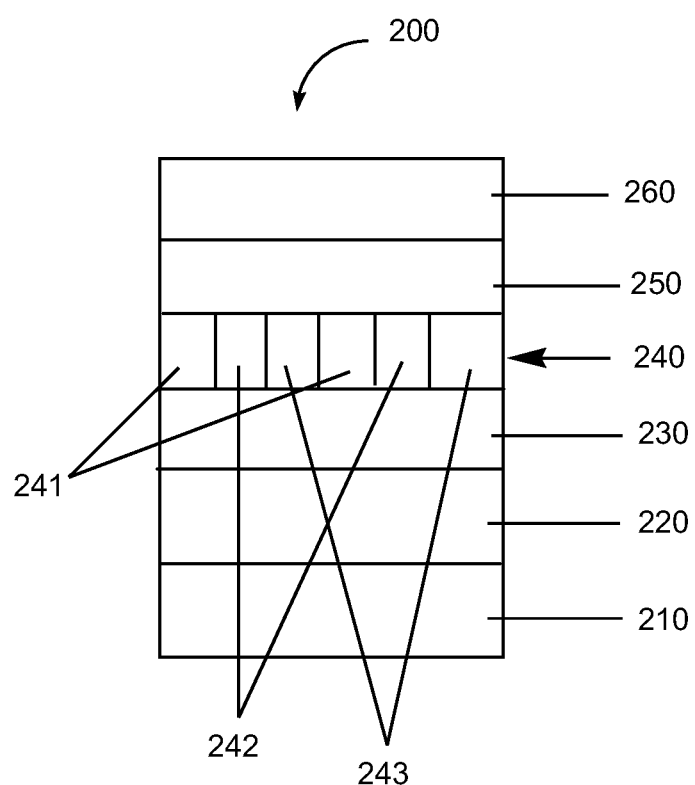
FIG. 3 includes a schematic diagram of another example of an organic electronic device.

In some embodiments, the electroactive layer 240 is pixellated, as shown in FIG. 3. Layer 240 is divided into pixel or subpixel units 241, 242, and 243 which are repeated over the layer. Each of the pixel or subpixel units represents a different color. In some embodiments, the subpixel units are for red, green, and blue. Although three subpixel units are shown in the figure, two or more than three may be used.

In one embodiment, the different layers have the following range of thicknesses: anode 210, 500-5000 Å, in one embodiment 1000-2000 Å; hole injection layer 220, 50-2000 Å, in one embodiment 200-1000 Å; hole transport layer 230, 50-2000 Å, in one embodiment 200-1000 Å; electroactive layer 240, 10-2000 Å, in one embodiment 100-1000 Å; layer 250, 50-2000 Å, in one embodiment 100-1000 Å; cathode 260, 200-10000 Å, in one embodiment 300-5000 Å. The location of the electron-hole recombination zone in the device, and thus the emission spectrum of the device, can be affected by the relative thickness of each layer. The desired ratio of layer thicknesses will depend on the exact nature of the materials used.

Depending upon the application of the device 200, the electroactive layer 240 can be a light-emitting layer that is activated by an applied voltage (such as in a light-emitting diode or light-emitting electrochemical cell), or a layer of material that responds to radiant energy and generates a signal with or without an applied bias voltage (such as in a photodetector). Examples of photodetectors include photoconductive cells, photoresistors, photoswitches, phototransistors, and phototubes, and photovoltaic cells, as these terms are described in Markus, John, *Electronics and Nucleonics Dictionary*, 470 and 476 (McGraw-Hill, Inc. 1966). Devices with light-emitting layers may be used to form displays or for lighting applications, such as white light luminaires.

One or more of the new deuterated materials described herein may be present in one or more of the active layers of a device. The deuterated materials may be used alone or in combination with non-deuterated or other deuterated materials.

In some embodiments, the new deuterated compounds are useful as hole transport materials in layer 230. In some embodiments, at least one additional layer includes a new deuterated material. In some embodiments, the additional layer is the hole injection layer 220. In some embodiments, the additional layer is the electroactive layer 240. In some embodiments, the additional layer is the electron transport layer 250.

In some embodiments, the new deuterated compounds are useful as host materials for electroactive dopant materials in electroactive layer 240. In some embodiments, the emissive material is also deuterated. In some embodiments, at least one additional layer includes a deuterated material. In some embodiments, the additional layer is the hole injection layer 220. In some embodiments, the additional layer is the hole transport layer 230. In some embodiments, the additional layer is the electron transport layer 250

In some embodiments, the new deuterated compounds are useful as electron transport materials in layer 250. In some embodiments, at least one additional layer includes a deuterated material. In some embodiments, the additional layer is the hole injection layer 220. In some embodiments, the additional layer is the hole transport layer 230. In some embodiments, the additional layer is the electroactive layer 240.

In some embodiments, an electronic device has deuterated materials in any combination of layers selected from the group consisting of the hole injection layer, the hole transport layer, the electroactive layer, and the electron transport layer.

In some embodiments, the devices have additional layers to aid in processing or to improve functionality. Any or all of these layers can include deuterated materials. In some embodiments, all the organic device layers comprise deuterated materials. In some embodiments, all the organic device layers consist essentially of deuterated materials.

Electroactive Layer

In some embodiments, the new deuterated compounds are useful as host materials. The electroactive layer comprises (a) an indolocarbazole compound having at least one deuterium substituent and (b) an electroactive dopant capable of electroluminescence having an emission maximum between 380 and 750 nm. The deuterated indolocarbazole compounds can be used alone, or in combination with a second host material. The new deuterated compounds can be used as a host for dopants with any color of emission. In some embodiments, the new deuterated compounds are used as hosts for green- or red-emissive materials. In some embodiments, the new deuterated compounds are used as hosts for organometallic electroluminescent materials.

In some embodiments, the electroactive layer consists essentially of a deuterated indolocarbazole compound host material and one or more electroactive dopants. In some embodiments, the electroactive layer consists essentially of a host material having Formula I or Formula II and an organometallic electroluminescent material. In some embodiments, the electroactive layer consists essentially of a first host material having Formula I, a second host material, and an electroactive dopant. Examples of second host materials include, but are not limited to, chrysenes, phenanthrenes, triphenylenes, phenanthrolines, naphthalenes, anthracenes, quinolines, isoquinolines, quinoxalines, phenylpyridines, benzodifurans, and metal quinolinate complexes.

The amount of dopant present in the electroactive composition is generally in the range of 3-20% by weight, based on the total weight of the composition; in some embodiments, 5-15% by weight. When a second host is present, the ratio of first host having Formula I or Formula II to second host is generally in the range of 1:20 to 20:1; in some embodiments, 5:15 to 15:5. In some embodiments, the first host material having Formula I is at least 50% by weight of the total host material; in some embodiments, at least 70% by weight.

Electroluminescent ("EL") materials which can be used as a dopant in the electroactive layer, include, but are not limited to, small molecule organic luminescent compounds, luminescent metal complexes, conjugated polymers, and mixtures thereof. Examples of small molecule luminescent compounds include, but are not limited to, chrysenes, pyrenes, perylenes, rubrenes, coumarins, anthracenes, thiadiazoles, derivatives thereof, and mixtures thereof. Examples of metal complexes include, but are not limited to, metal chelated oxinoid compounds and cyclometallated complexes of metals such as iridium and platinum. Examples of conjugated polymers include, but are not limited to poly(phenylenevinylenes), polyfluorenes, poly(spirobifluorenes), polythiophenes, poly(p-phenylenes), copolymers thereof, and mixtures thereof.

Examples of red light-emitting materials include, but are not limited to, cyclometalated complexes of Ir having phenylquinoline or phenylisoquinoline ligands, periflanthenes, fluoranthenes, and perylenes. Red light-emitting materials have been disclosed in, for example, U.S. Pat. No. 6,875,524, and published US application 2005-0158577.

Examples of green light-emitting materials include, but are not limited to, cyclometalated complexes of Ir having phenylpyridine ligands, bis(diarylamino)anthracenes, and polyphenylenevinylene polymers. Green light-emitting materials have been disclosed in, for example, published PCT application WO 2007/021117.

Examples of blue light-emitting materials include, but are not limited to, diarylanthracenes, diaminochrysenes, diaminopyrenes, and polyfluorene polymers. Blue light-emitting materials have been disclosed in, for example, U.S. Pat. No. 6,875,524, and published US applications 2007-0292713 and 2007-0063638.

In some embodiments, the dopant is an organometallic complex. In some embodiments, the dopant is a cyclometalated complex of iridium or platinum. Such materials have been disclosed in, for example, U.S. Pat. No. 6,670,645 and Published PCT Applications WO 03/063555, WO 2004/016710, and WO 03/040257.

In some embodiments, the dopant is a complex having the formula $Ir(L1)_a(L2)_b(L3)_c$; where
  L1 is a monoanionic bidentate cyclometalating ligand coordinated through carbon and nitrogen;
  L2 is a monoanionic bidentate ligand which is not coordinated through a carbon;
  L3 is a monodentate ligand;
  a is 1-3;
  b and c are independently 0-2; and
  a, b, and c are selected such that the iridium is hexacoordinate and the complex is electrically neutral.
Some examples of formulae include, but are not limited to, $Ir(L1)_3$; $Ir(L1)_2(L2)$; and $Ir(L1)_2(L3)(L3')$, where L3 is anionic and L3' is nonionic.

Examples of L1 ligands include, but are not limited to phenylpyridines, phenylquinolines, phenylpyrimidines, phenylpyrazoles, thienylpyridines, thienylquinolines, and thienylpyrimidines. As used herein, the term "quinolines" includes "isoquinolines" unless otherwise specified. The fluorinated derivatives can have one or more fluorine substituents. In some embodiments, there are 1-3 fluorine substituents on the non-nitrogen ring of the ligand.

Monoanionic bidentate ligands, L2, are well known in the art of metal coordination chemistry. In general these ligands have N, O, P, or S as coordinating atoms and form 5- or 6-membered rings when coordinated to the iridium. Suitable coordinating groups include amino, imino, amido, alkoxide, carboxylate, phosphino, thiolate, and the like. Examples of suitable parent compounds for these ligands include β-dicarbonyls (β-enolate ligands), and their N and S analogs; amino carboxylic acids (aminocarboxylate ligands); pyridine carboxylic acids (iminocarboxylate ligands); salicylic acid derivatives (salicylate ligands); hydroxyquinolines (hydroxyquinolinate ligands) and their S analogs; and phosphinoalkanols (phosphinoalkoxide ligands).

Monodentate ligand L3 can be anionic or nonionic. Anionic ligands include, but are not limited to, H⁻ ("hydride") and ligands having C, O or S as coordinating atoms. Coordinating groups include, but are not limited to alkoxide, carboxylate, thiocarboxylate, dithiocarboxylate, sulfonate, thiolate, carbamate, dithiocarbamate, thiocarbazone anions, sulfonamide anions, and the like. In some cases, ligands listed above as L2, such as β-enolates and phosphinoakoxides, can act as monodentate ligands. The monodentate ligand can also be a coordinating anion such as halide, cyanide, isocyanide, nitrate, sulfate, hexahaloantimonate, and the like. These ligands are generally available commercially.

The monodentate L3 ligand can also be a non-ionic ligand, such as CO or a monodentate phosphine ligand.

In some embodiments, one or more of the ligands has at least one substituent selected from the group consisting of F and fluorinated alkyls.

The iridium complex dopants can be made using standard synthetic techniques as described in, for example, U.S. Pat. No. 6,670,645.

Examples of organometallic iridium complexes having red emission color include, but are not limited to compounds D1 through D10 below.

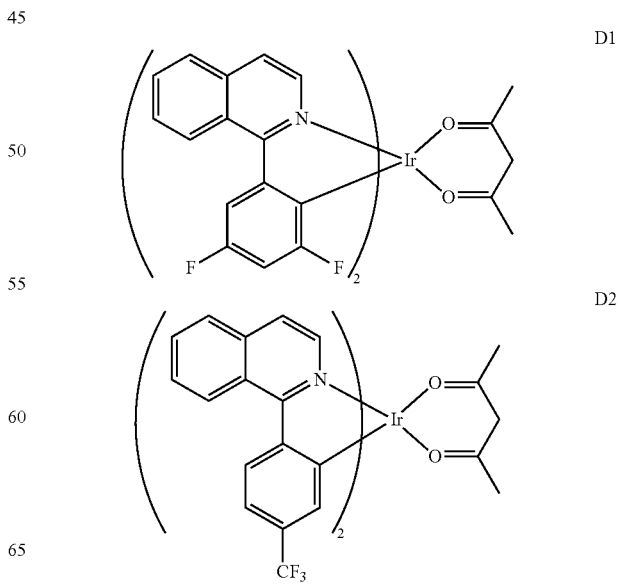

-continued
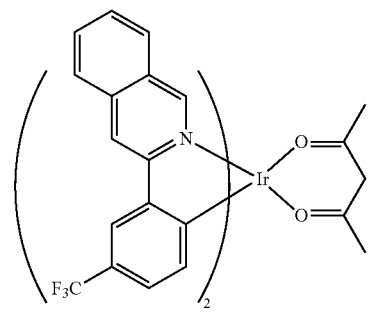
D3
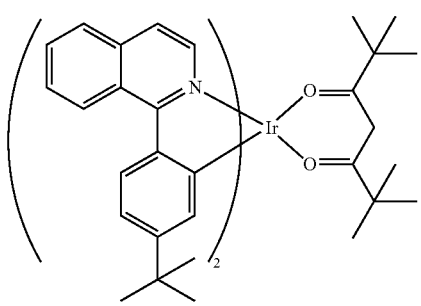
D4
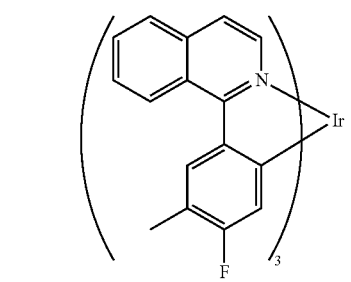
D5
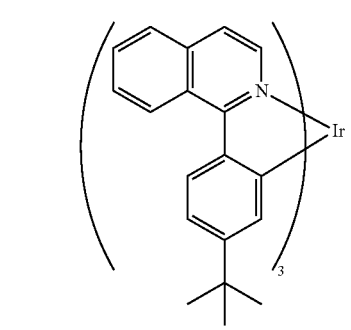
D6
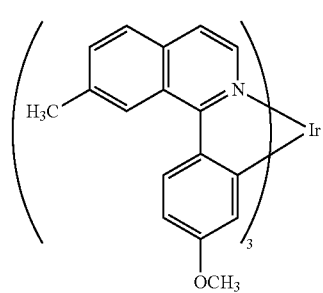
D7
-continued
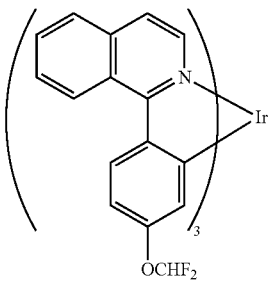
D8
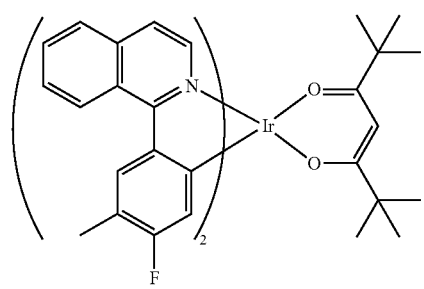
D9
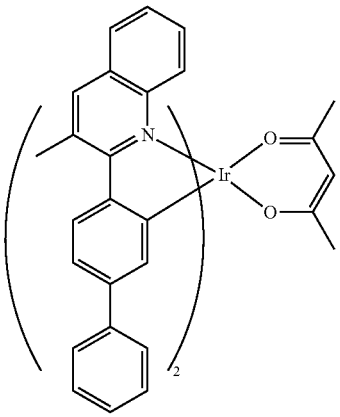
D10
Examples of organometallic Ir complexes with green emission color include, but are not limited to, D11 through D33 below.
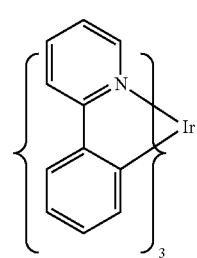
D11

-continued
D12
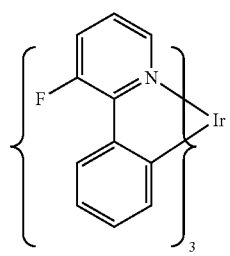
D13
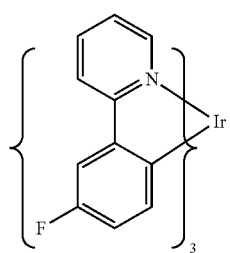
D14
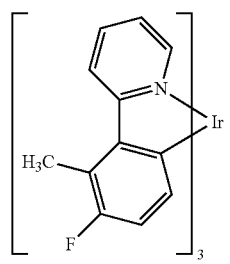
D15
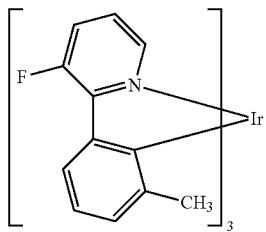
D16
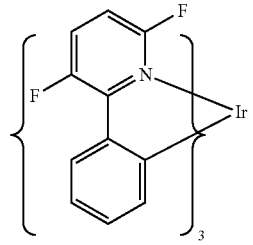
D17
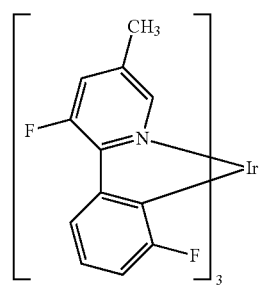
-continued
D18
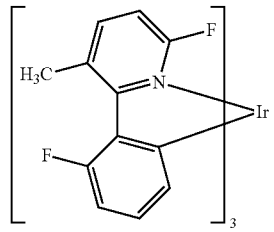
D19
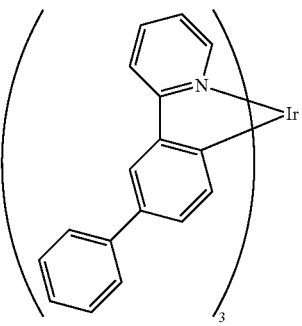
D21
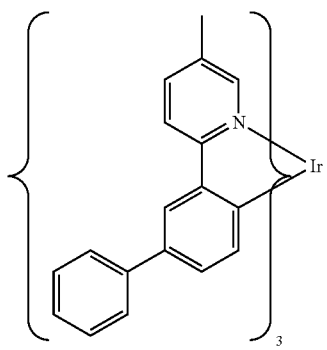
D22
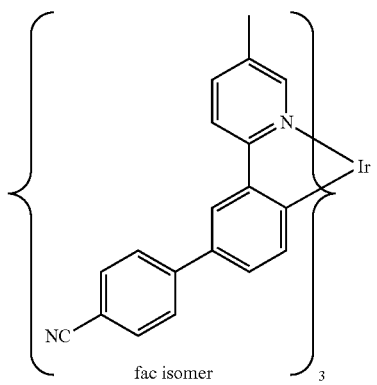
fac isomer
D23
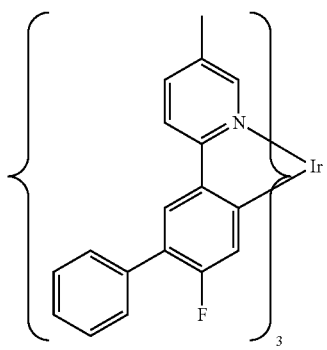

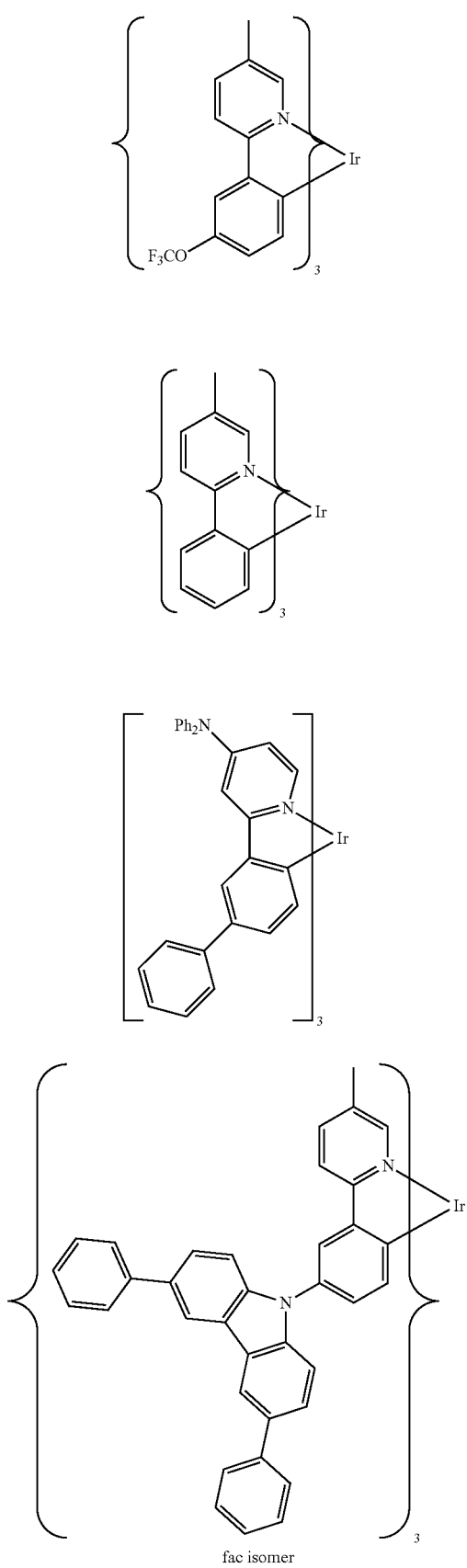
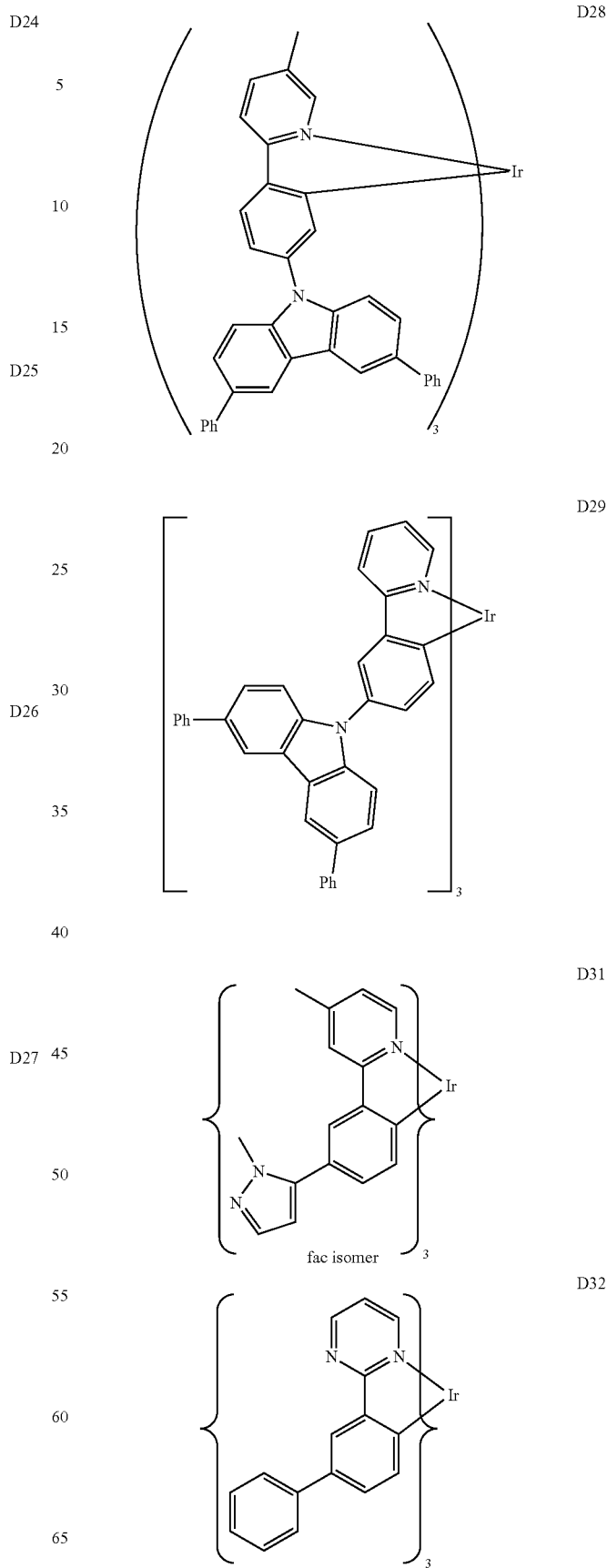

-continued

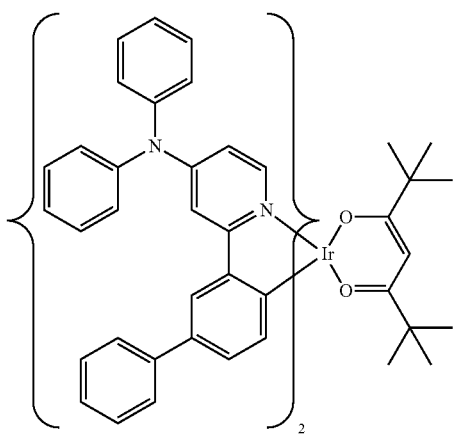

D33

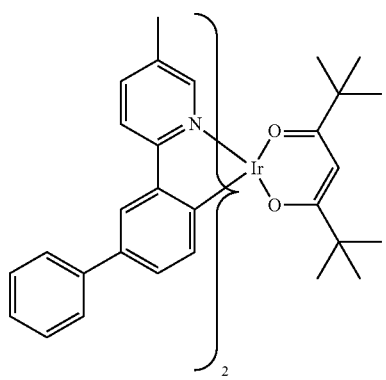

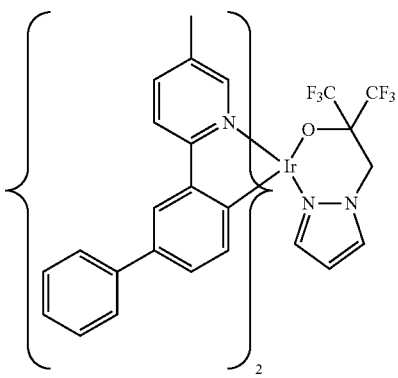

In some embodiments, the dopant is an small organic luminescent compound. In some embodiments, the dopant is selected from the group consisting of a non-polymeric spirobifluorene compound and a fluoranthene compound.

In some embodiments, the dopant is a compound having aryl amine groups. In some embodiments, the electroactive dopant is selected from the formulae below:

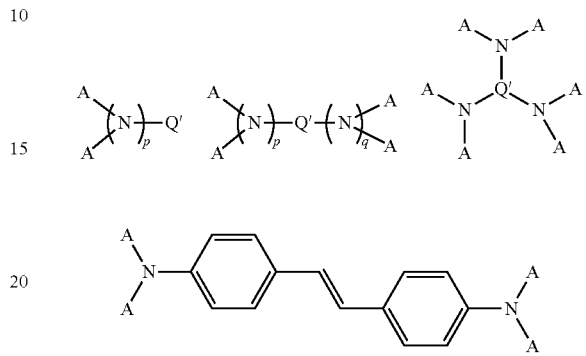

where:

A is the same or different at each occurrence and is an aromatic group having from 3-60 carbon atoms;

Q' is a single bond or an aromatic group having from 3-60 carbon atoms;

p and q are independently an integer from 1-6.

In some embodiments of the above formula, at least one of A and Q' in each formula has at least three condensed rings. In some embodiments, p and q are equal to 1.

In some embodiments, Q' is a styryl or styrylphenyl group.

In some embodiments, Q' is an aromatic group having at least two condensed rings. In some embodiments, Q' is selected from the group consisting of naphthalene, anthracene, chrysene, pyrene, tetracene, xanthene, perylene, coumarin, rhodamine, quinacridone, and rubrene.

In some embodiments, A is selected from the group consisting of phenyl, biphenyl, tolyl, naphthyl, naphthylphenyl, and anthracenyl groups.

In some embodiments, the dopant has the formula below:

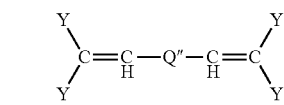

where:

Y is the same or different at each occurrence and is an aromatic group having 3-60 carbon atoms;

Q" is an aromatic group, a divalent triphenylamine residue group, or a single bond.

In some embodiments, the dopant is an aryl acene. In some embodiments, the dopant is a non-symmetrical aryl acene.

Some examples of small molecule organic green dopants include, but are not limited to, compounds D34 through D41 shown below.

D34
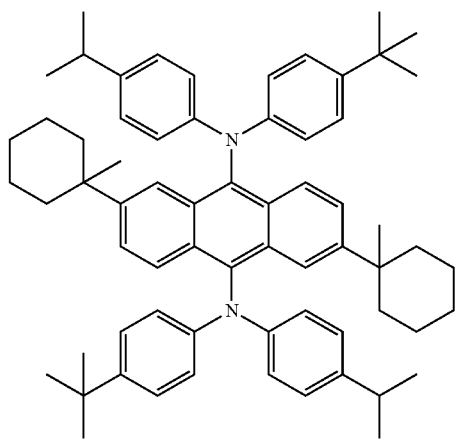
D35
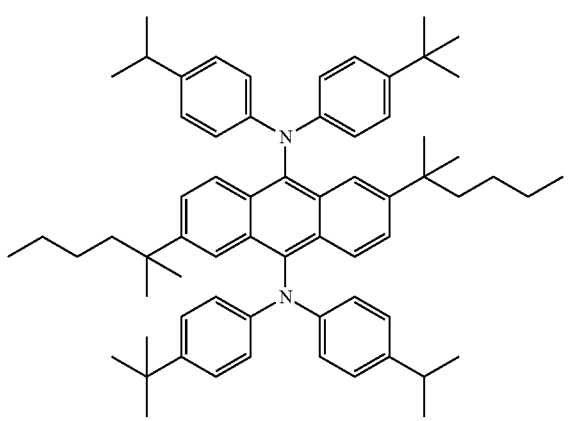
D36
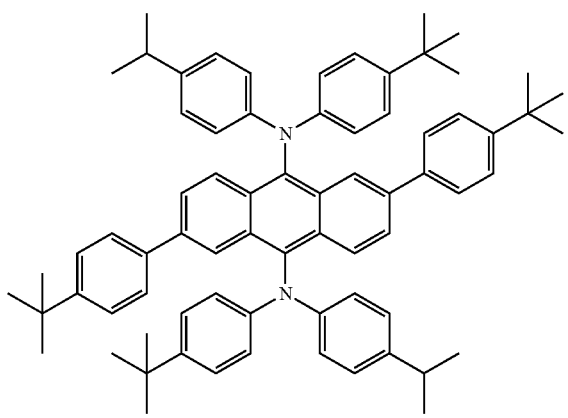
D37
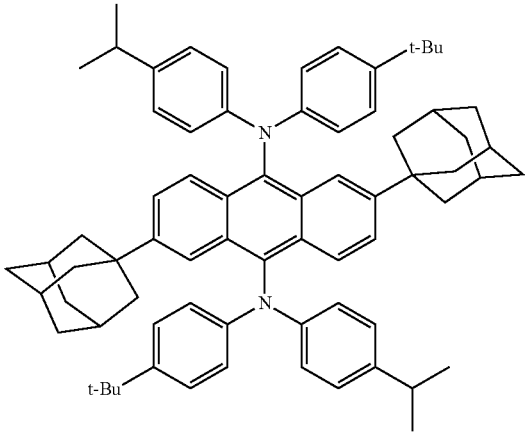
D38
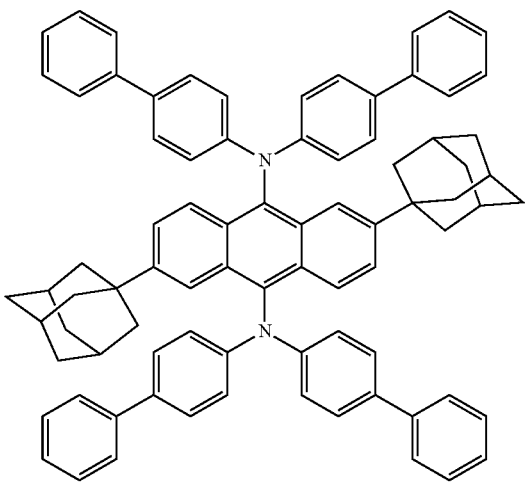
D39
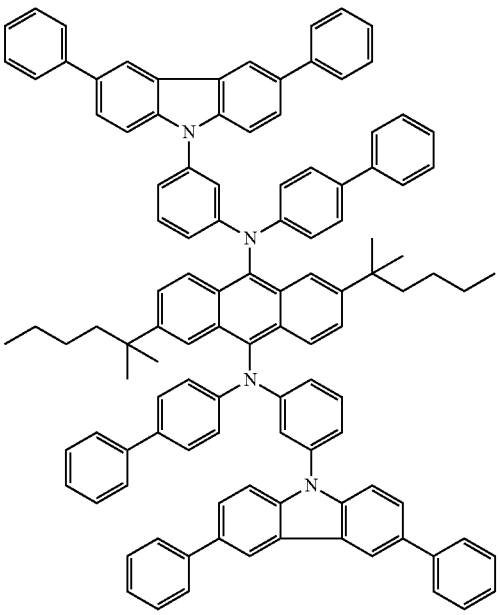

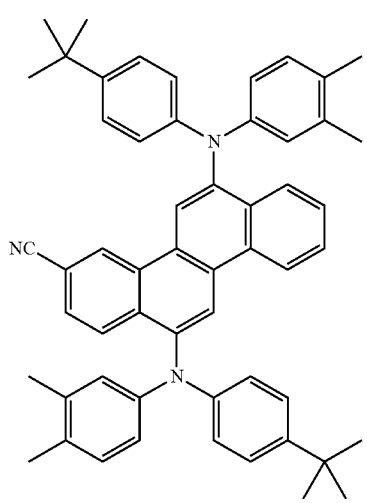
D40
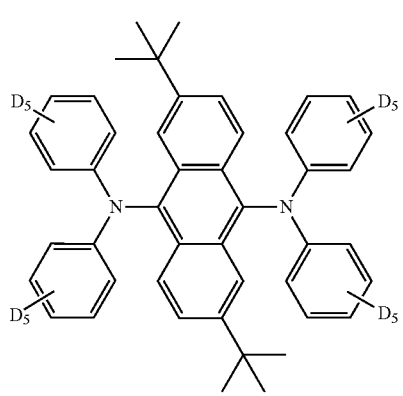
D41
Examples of small molecule organic blue dopants include, but are not limited to compounds D42 through D49 shown below.
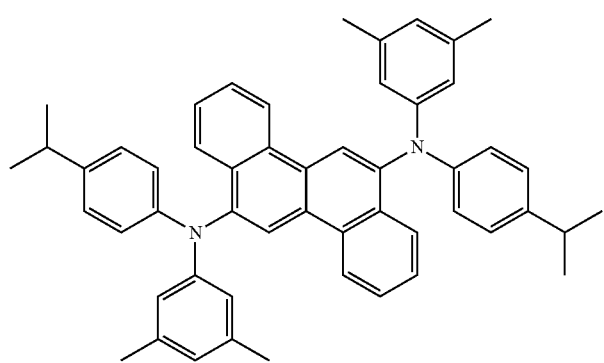
D42
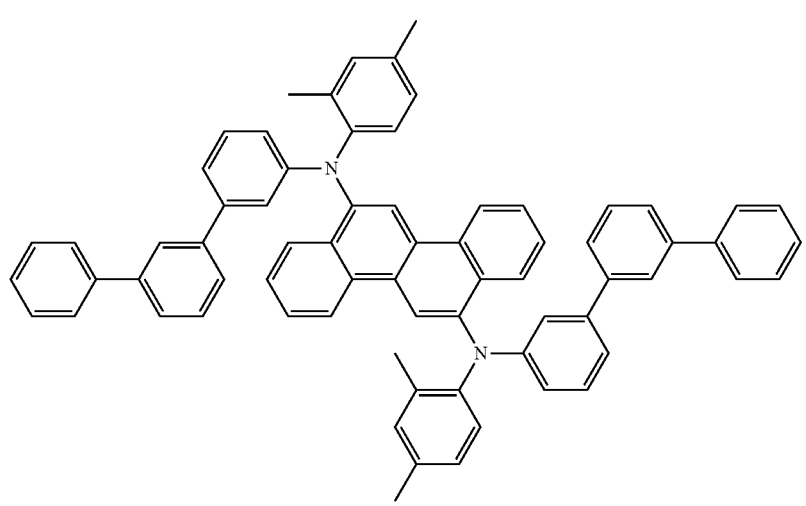
D43

-continued
D44
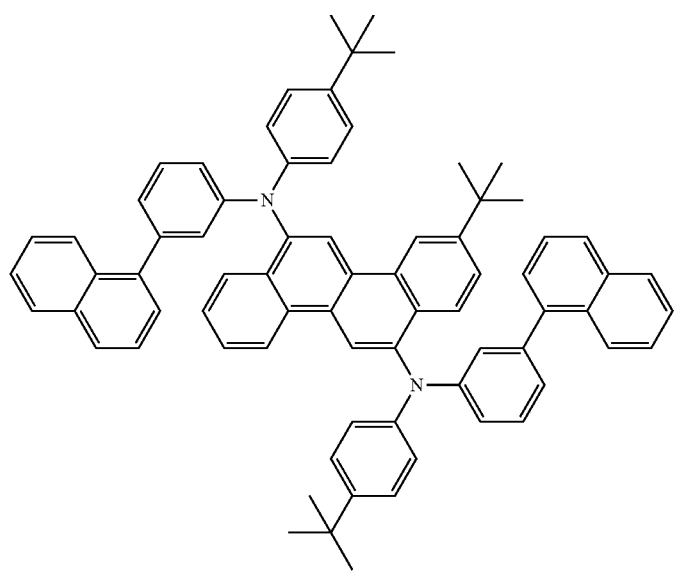
D45
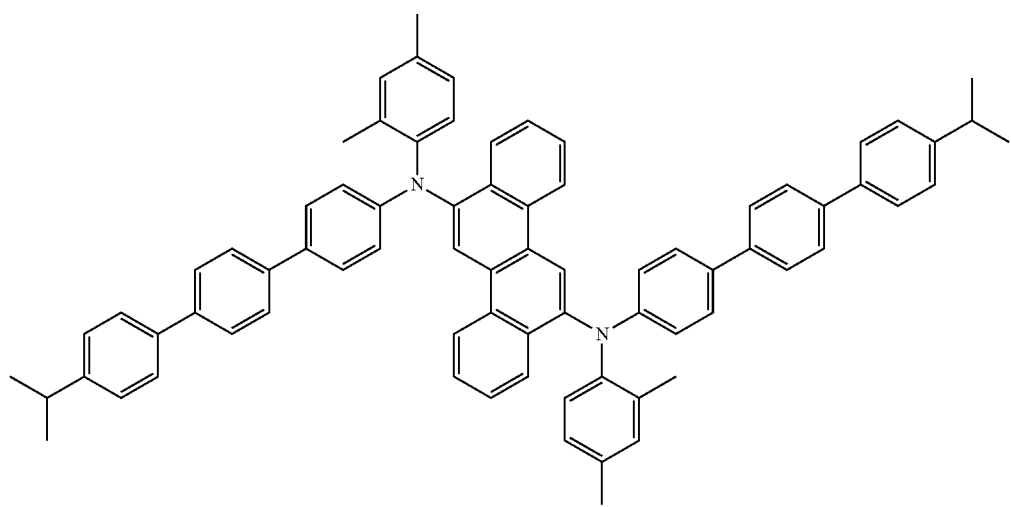

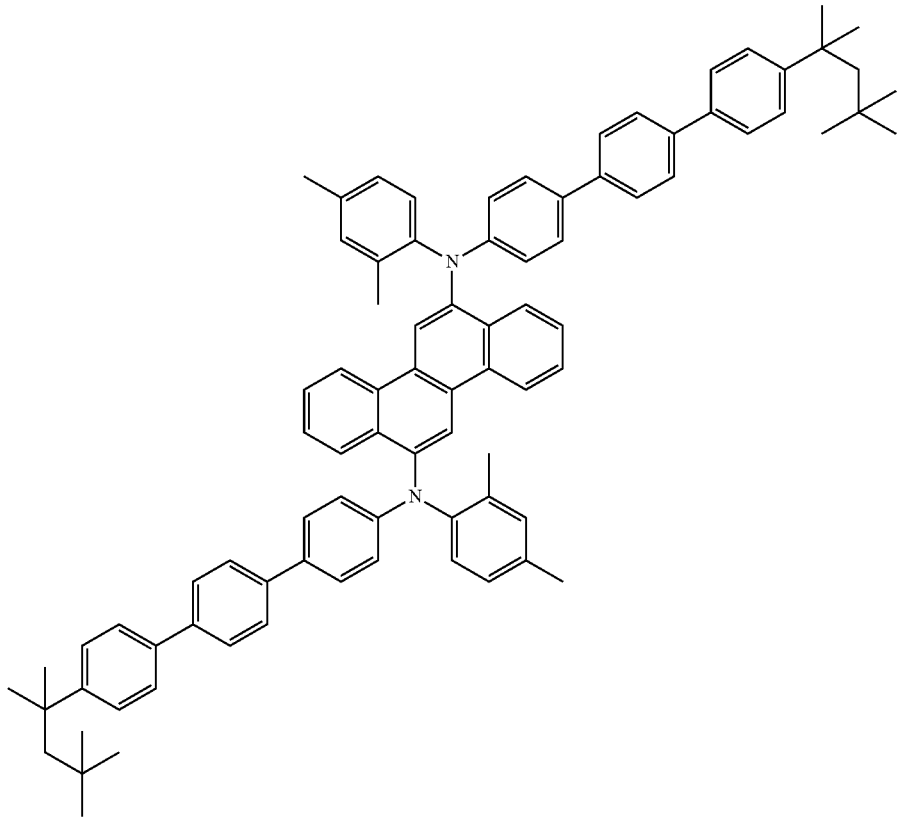
D46
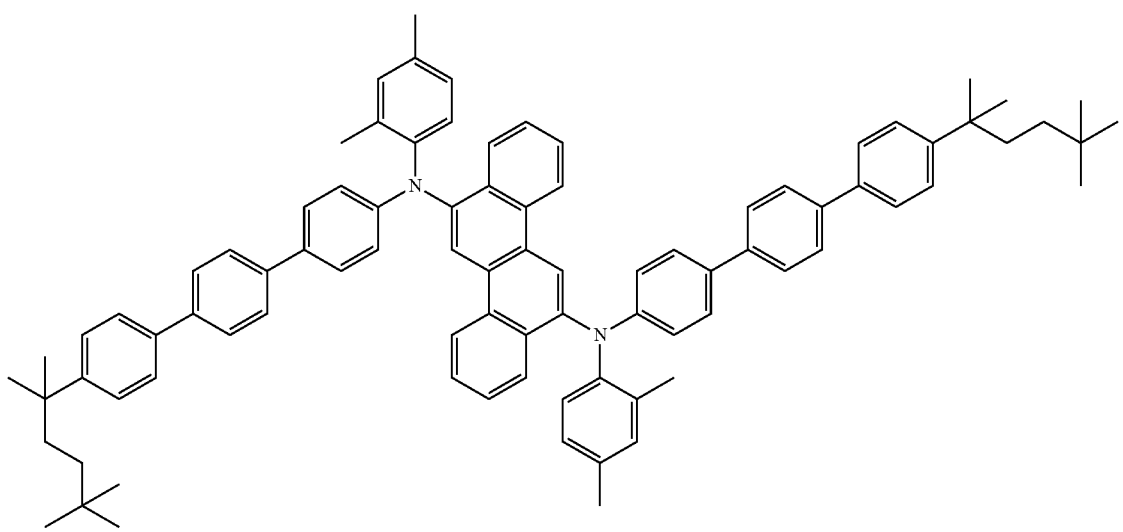
D47

-continued

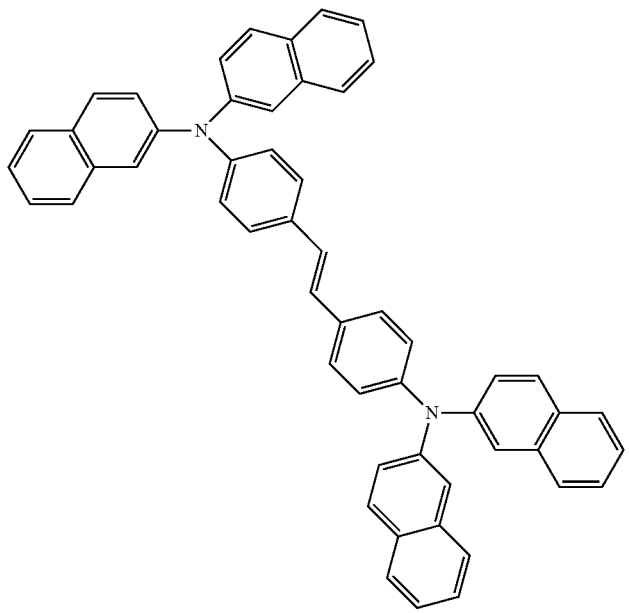
D48

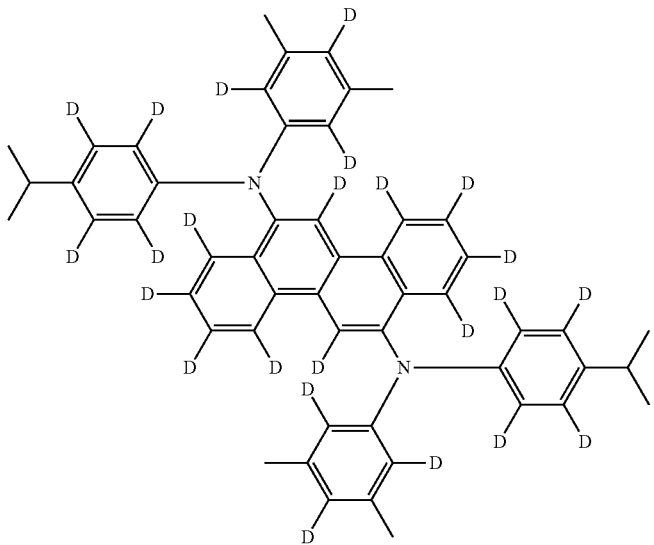
D49

In some embodiments, the electroactive dopant is selected from the group consisting of amino-substituted chrysenes and amino-substituted anthracenes.

In some embodiments, the new deuterated compound described herein is an electroluminescent material and is present as an electroactive material.

Other Device Layers

The other layers in the device can be made of any materials that are known to be useful in such layers.

The anode 210, is an electrode that is particularly efficient for injecting positive charge carriers. It can be made of, for example, materials containing a metal, mixed metal, alloy, metal oxide or mixed-metal oxide, or it can be a conducting polymer, or mixtures thereof. Suitable metals include the Group 11 metals, the metals in Groups 4-6, and the Group 8-10 transition metals. If the anode is to be light-transmitting, mixed-metal oxides of Groups 12, 13 and 14 metals, such as indium-tin-oxide, are generally used. The anode 210 can also comprise an organic material such as polyaniline as described in "Flexible light-emitting diodes made from soluble conducting polymer," Nature vol. 357, pp 477-479 (11 Jun. 1992). At least one of the anode and cathode is desirably at least partially transparent to allow the generated light to be observed.

The hole injection layer 220 comprises hole injection material and may have one or more functions in an organic electronic device, including but not limited to, planarization of the underlying layer, charge transport and/or charge injection properties, scavenging of impurities such as oxygen or metal ions, and other aspects to facilitate or to improve the performance of the organic electronic device. Hole injection materials may be polymers, oligomers, or small molecules. They may be vapour deposited or deposited from liquids which may be in the form of solutions, dispersions, suspensions, emulsions, colloidal mixtures, or other compositions.

The hole injection layer can be formed with polymeric materials, such as polyaniline (PANI) or polyethylenedioxythiophene (PEDOT), which are often doped with protonic acids. The protonic acids can be, for example, poly(styrenesulfonic acid), poly(2-acrylamido-2-methyl-1-propanesulfonic acid), and the like.

The hole injection layer can comprise charge transfer compounds, and the like, such as copper phthalocyanine and the tetrathiafulvalene-tetracyanoquinodimethane system (TTF-TCNQ).

In some embodiments, the hole injection layer comprises at least one electrically conductive polymer and at least one fluorinated acid polymer. Such materials have been described in, for example, published U.S. patent applications 2004-0102577, 2004-0127637, and 2005/205860

In some embodiments, the hole transport layer 230 comprises the new deuterated indolocarbazole compound. Examples of other hole transport materials for layer 230 have been summarized for example, in Kirk-Othmer Encyclopedia of Chemical Technology, Fourth Edition, Vol. 18, p. 837-860, 1996, by Y. Wang. Both hole transporting molecules and polymers can be used. Commonly used hole transporting molecules are: N,N'-diphenyl-N,N'-bis(3-methylphenyl)-[1,1'-biphenyl]-4,4'-diamine (TPD), 1,1-bis[(di-4-tolylamino) phenyl]cyclohexane (TAPC), N,N'-bis(4-methylphenyl)-N,N'-bis(4-ethylphenyl)-[1,1'-(3,3'-dimethyl) biphenyl]-4,4'-diamine (ETPD), tetrakis-(3-methylphenyl)-N,N,N',N'-2,5-phenylenediamine (PDA), a-phenyl-4-N,N-diphenylaminostyrene (TPS), p-(diethylamino) benzaldehyde diphenylhydrazone (DEH), triphenylamine (TPA), bis[4-(N,N-diethylamino)-2-methylphenyl](4-methylphenyl)methane (MPMP), 1-phenyl-3-[p-(diethylamino) styryl]-5-[p-(diethylamino)phenyl]pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), N,N'-bis(naphthalen-1-yl)-N,N'-bis-(phenyl)benzidine (—NPB), and porphyrinic compounds, such as copper phthalocyanine. Commonly used hole transporting polymers are polyvinylcarbazole, (phenylmethyl)-polysilane, and polyaniline. It is also possible to obtain hole transporting polymers by doping hole transporting molecules such as those mentioned above into polymers such as polystyrene and polycarbonate. In some cases, triarylamine polymers are used, especially triarylamine-fluorene copolymers. In some cases, the polymers and copolymers are crosslinkable. Examples of crosslinkable hole transport polymers can be found in, for example, published US patent application 2005-0184287 and published PCT application WO 2005/052027. In some embodiments, the hole transport layer is doped with a p-dopant, such as tetrafluorotetracyanoquinodimethane and perylene-3,4,9,10-tetracarboxylic-3,4,9,10-dianhydride.

In some embodiments, the electron transport layer 250 comprises the new deuterated indolocarbazole compound. Examples of other electron transport materials which can be used in layer 250 include metal chelated oxinoid compounds, such as tris(8-hydroxyquinolato)aluminum (Alq$_3$); bis(2-methyl-8-quinolinolato)(para-phenyl-phenolato)aluminum(III) (BAlQ); and azole compounds such as 2-(4-biphenylyl)-5-(4-t-butylphenyl)-1,3,4-oxadiazole (PBD) and 3-(4-biphenylyl)-4-phenyl-5-(4-t-butylphenyl)-1,2,4-triazole (TAZ), and 1,3,5-tri(phenyl-2-benzimidazole)benzene (TPBI); quinoxaline derivatives such as 2,3-bis(4-fluorophenyl)quinoxaline; phenanthroline derivatives such as 9,10-diphenylphenanthroline (DPA) and 2,9-dimethyl-4,7-diphenyl-1,10-phenanthroline (DDPA); and mixtures thereof. The electron-transport layer may also be doped with n-dopants, such as Cs or other alkali metals. Layer 250 can function both to facilitate electron transport, and also serve as a buffer layer or confinement layer to prevent quenching of the exciton at layer interfaces. Preferably, this layer promotes electron mobility and reduces exciton quenching.

The cathode 260, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used. Li- or Cs-containing organometallic compounds, LiF, CsF, and Li$_2$O can also be deposited between the organic layer and the cathode layer to lower the operating voltage.

It is known to have other layers in organic electronic devices. For example, there can be a layer (not shown) between the anode 210 and hole injection layer 220 to control the amount of positive charge injected and/or to provide band-gap matching of the layers, or to function as a protective layer. Layers that are known in the art can be used, such as copper phthalocyanine, silicon oxy-nitride, fluorocarbons, silanes, or an ultra-thin layer of a metal, such as Pt. Alternatively, some or all of anode layer 210, active layers 220, 230, 240, and 250, or cathode layer 260, can be surface-treated to increase charge carrier transport efficiency. The choice of materials for each of the component layers is preferably determined by balancing the positive and negative charges in the emitter layer to provide a device with high electroluminescence efficiency.

It is understood that each functional layer can be made up of more than one layer.

The device can be prepared by a variety of techniques, including sequential vapor deposition of the individual layers on a suitable substrate. Substrates such as glass, plastics, and metals can be used. Conventional vapor deposition techniques can be used, such as thermal evaporation, chemical vapor deposition, and the like. Alternatively, the organic layers can be applied from solutions or dispersions in suitable solvents, using conventional coating or printing techniques, including but not limited to spin-coating, dip-coating, roll-to-roll techniques, ink-jet printing, screen-printing, gravure printing and the like.

To achieve a high efficiency LED, the HOMO (highest occupied molecular orbital) of the hole transport material desirably aligns with the work function of the anode, and the LUMO (lowest un-occupied molecular orbital) of the electron transport material desirably aligns with the work function of the cathode. Chemical compatibility and sublimation temperature of the materials are also important considerations in selecting the electron and hole transport materials.

It is understood that the efficiency of devices made with the indolocarbazole compounds described herein, can be further improved by optimizing the other layers in the device. For example, more efficient cathodes such as Ca, Ba or LiF can be used. Shaped substrates and novel hole transport materials that result in a reduction in operating voltage or increase quantum efficiency are also applicable. Additional layers can also be added to tailor the energy levels of the various layers and facilitate electroluminescence.

EXAMPLES

The following examples illustrate certain features and advantages of the present invention. They are intended to be illustrative of the invention, but not limiting. All percentages are by weight, unless otherwise indicated.

Synthesis Example 1

This example illustrates the preparation of a deuterated indolocarbazole compound.

Compound H1 was made from the non-deuterated analog, Comparative Compound A, shown below.

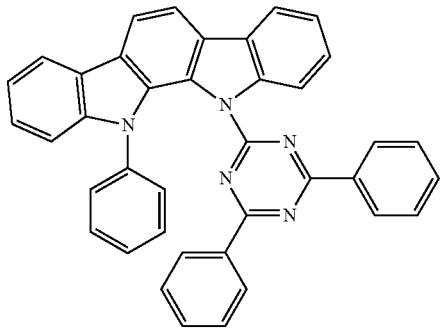

Comparative Compound A

Comparative Compound A was made as described in published European Patent Application EP 2080762, Example 1.

Comparative Compound A (1 g, 1.8 mmol) was dissolved in 19.6 mL $C_6D_6$ in a 100-mL round bottom flask and deuterated triflic acid (1.34 g, 8.9 mmol) added to it. The resulting dark red solution was stirred at 50° C. for 5 hours. The reaction was quenched with a $D_2O$ solution of $Na_2CO_3$. The layers were separated and the organic layer washed with two 30-mL portions of water. The combined aqueous layers were extracted with 30-mL methylene chloride and then dried over $Na_2SO_4$, filtered and concentrated to dryness. Further purification by column chromatography over silica gel (methylene chloride-hexanes) afforded 0.62 g (62%, 99.99% pure) of a bright yellow solid.

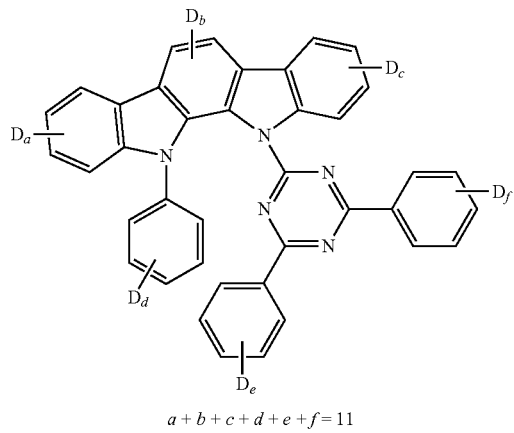

Compound H1

$a + b + c + d + e + f = 11$

Device Example 1 and Comparative Device Example A

These examples demonstrate the fabrication and performance of a device with an organometallic iridium complex as a green dopant, D21. The dopant was made using a procedure similar to those described in U.S. Pat. No. 6,670,645.

The device had the following structure on a glass substrate:
anode=Indium Tin Oxide (ITO): 50 nm
hole injection layer=HIJ1 (50 nm), which is an aqueous dispersion of an electrically conductive polymer and a polymeric fluorinated sulfonic acid. Such materials have been described in, for example, published U.S. patent applications US 2004/0102577, US 2004/0127637, US 2005/0205860, and published PCT application WO 2009/018009.
hole transport layer=polymer P1, which is a non-cross-linked arylamine polymer (20 nm)
electroactive layer=13:1 host:dopant, as shown in Table 1
electron transport layer=ET1, which is a metal quinolate derivative (10 nm)
cathode=CsF/Al (1.0/100 nm)

TABLE 1

Device Electroactive Layers

| Example | Host | Dopant | Thickness |
|---|---|---|---|
| Comparative A-1 | Comp. Compound A | D21 | 53 nm |
| Comparative A-2 | Comp. Compound A | D21 | 53 nm |
| Comparative A-3 | Comp. Compound A | D21 | 53 nm |
| Ex. 1-1 | H1 | D21 | 56 nm |
| Ex. 1-2 | H1 | D21 | 56 nm |
| Ex. 1-3 | H1 | D21 | 56 nm |

OLED devices were fabricated by a combination of solution processing and thermal evaporation techniques. Patterned indium tin oxide (ITO) coated glass substrates from Thin Film Devices, Inc were used. These ITO substrates are based on Corning 1737 glass coated with ITO having a sheet resistance of 30 ohms/square and 80% light transmission. The patterned ITO substrates were cleaned ultrasonically in aqueous detergent solution and rinsed with distilled water. The patterned ITO was subsequently cleaned ultrasonically in acetone, rinsed with isopropanol, and dried in a stream of nitrogen.

Immediately before device fabrication the cleaned, patterned ITO substrates were treated with UV ozone for 10 minutes. Immediately after cooling, an aqueous dispersion of HIJ1 was spin-coated over the ITO surface and heated to remove solvent. After cooling, the substrates were then spin-coated with a solution of a hole transport material, and then heated to remove solvent. After cooling the substrates were spin-coated with the emissive layer solution, and heated to remove solvent. The substrates were masked and placed in a vacuum chamber. The electron transport layer was deposited by thermal evaporation, followed by a layer of CsF. Masks were then changed in vacuo and a layer of Al was deposited by thermal evaporation. The chamber was vented, and the devices were encapsulated using a glass lid, desiccant, and UV curable epoxy.

The OLED samples were characterized by measuring their (1) current-voltage (I-V) curves, (2) electroluminescence radiance versus voltage, and (3) electroluminescence spectra versus voltage. All three measurements were performed at the same time and controlled by a computer. The current efficiency of the device at a certain voltage is determined by dividing the electroluminescence radiance of the LED by the current needed to run the device. The unit is a cd/A. The power efficiency is the current efficiency multiplied by pi, divided by the operating voltage. The unit is lm/W. The device data is given in Table 2.

TABLE 2

Device Performance

| Ex. | CIE (x, y) | Voltage (V) | C.E. (cd/A) | E.Q.E. (%) | P.E. (lm/W) | Lifetest current density (mA/cm2) | Lifetest Luminance (nits) | Raw T50 (h) | Projected Lifetime T50 @1000 nits |
|---|---|---|---|---|---|---|---|---|---|
| Comp. A-1 | 0.304, 0.637 | 3.4 | 49.5 | 13.8 | 45.8 | 131 | 13730 | 208 | 23220 |
| Comp. A-2 | 0.303, 0.638 | 3.3 | 52.0 | 14.4 | 48.9 | 130 | 14500 | 210 | 35863 |
| Comp. A-3 | 0.304, 0.638 | 3.4 | 51.8 | 14.3 | 48.0 | 129 | 13920 | 223 | 25519 |
| Ex. 1-1 | 0.307, 0.637 | 3.4 | 57.0 | 15.8 | 52.8 | 125 | 15060 | 340 | 44829 |
| Ex. 1-2 | 0.307, 0.637 | 3.4 | 58.6 | 16.2 | 54.1 | 131 | 16480 | 325 | 50397 |
| Ex. 1-3 | 0.310, 0.635 | 3.5 | 58.7 | 16.2 | 53.1 | 126 | 15600 | 360 | 50574 |

* All data @ 1000 nits, CE = current efficiency; CIEx and CIEy are the x and y color coordinates according to the C.I.E. chromaticity scale (Commisssion Internationale de L'Eclairage, 1931). Raw T50 is the time in hours for a device to reach one-half the initial luminance at the lifetest luminance given. Projected T50 is the projected lifetime at 1000 nits using an acceleration factor of 1.8.

It can be seen that with the deuterated indolocarbazole host of the invention, the lifetime of devices is greatly increased, while maintaining other device properties. The comparative devices with a non-deuterated host had an average projected T50 of 24,867 hours. With the deuterated host of the invention, H1, the devices had an average projected T50 of 48,600 hours.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

What is claimed is:

1. An indolocarbazole compound having Formula I or Formula II:

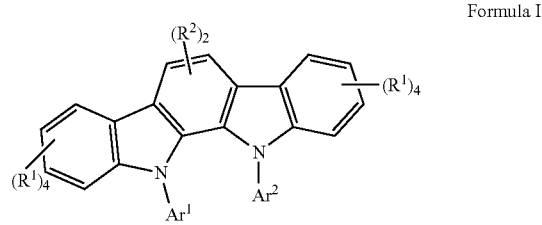

Formula I

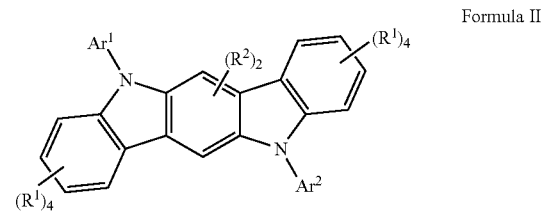

Formula II wherein:

Ar$^1$ is an aromatic electron transporting group;

Ar$^2$ is selected from the group consisting of aryl groups and aromatic electron transporting groups; and R$^1$ and R$^2$ are the same or different at each occurrence and are selected from the group consisting of H, D and aryl;

wherein the compound has at least one D.

2. The compound of claim 1, wherein Ar$^1$ is a nitrogen-containing heteroaromatic group.

3. The compound of claim 2, wherein the nitrogen-containing heteroaromatic group is selected from the group consisting of

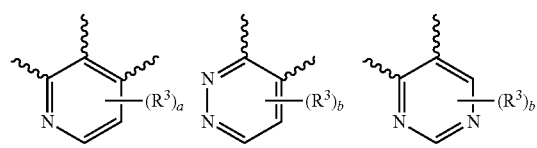

-continued

[chemical structures: pyrazine, triazine, triazine variants with (R³)_b, (R³)_c; quinoxaline, phenanthroline-type with (R³)_d, (R³)_a, (R³)_b; pyridoquinoline with (R³)_a, (R³)_b; oxadiazole with (R³)_e; oxadiazole with (R³)_e; benzimidazole with Ar³ and (R³)_a; isoquinoline with (R³)_f; quinoline with (R³)_f]

wherein:
Ar³ is an aryl group;
R³ is the same or different at each occurrence and is selected from the group consisting of D, alkyl, alkoxy, aryl, aryloxy, siloxane, and silyl;
a is an integer from 0-4;
b is an integer from 0-3;
c is an integer from 0-2;
d is an integer from 0-5;
e is 0 or 1;
f is an integer from 0-6; and
the nitrogen-containing heteroaromatic group can be bonded to the nitrogen on the indolocarbazole core at any of the positions indicated with the wavy line.

4. The compound of claim 3, wherein R³ is selected from D and aryl.

5. The compound of claim 1, wherein at least one of Ar² is selected from the group consisting of phenyl, naphthyl, phenanthryl, anthracenyl, phenylnaphthylene, naphthylphenylene, deuterated derivatives thereof, and a group having Formula III:

Formula III

[chemical structure showing phenyl rings with R⁴ substituents and (R⁴)₄, (R⁴)_m]

where:
R⁴ is the same or different at each occurrence and is selected from the group consisting of H, D, alkyl, alkoxy, siloxane and silyl, or adjacent R⁴ groups may be joined together to form an aromatic ring; and
m is the same or different at each occurrence and is an integer from 1 to 6.

6. The compound of claim 1, wherein R¹ and R² are aryl.

7. The compound of claim 1, wherein R¹ and R² are H or D.

8. The compound of claim 1, selected from Compounds H1 through H21

Compound H1

[chemical structure of indolocarbazole with triazine substituent, showing D_a, D_b, D_c, D_d, D_e, D_f labels]

Σ(a-f) = 1-25

Compound H2

[chemical structure of indolocarbazole with pyridyl-pyridine substituent, showing D_a, D_b, D_c, D_d, D_e, D_f labels]

Σ(a-f) = 1-24

Compound H3
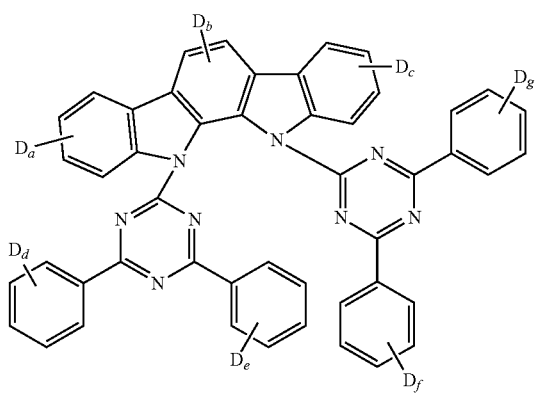
Σ(a-g) = 1-30
Compound H4
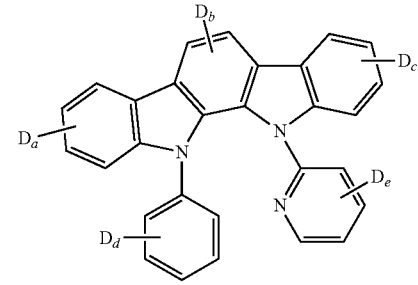
Σ(a-e) = 1-19
Compound H5
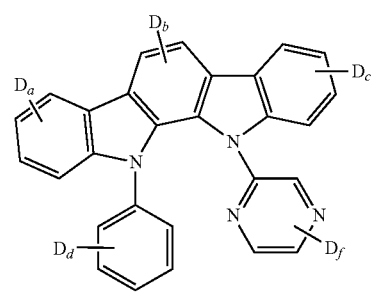
Σ(a-f) = 1-18
Compound H6
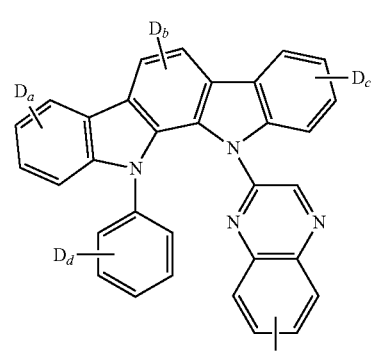
Σ(a-f) = 1-20
Compound H7
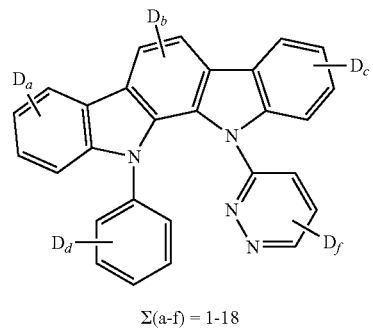
Σ(a-f) = 1-18
Compound H8
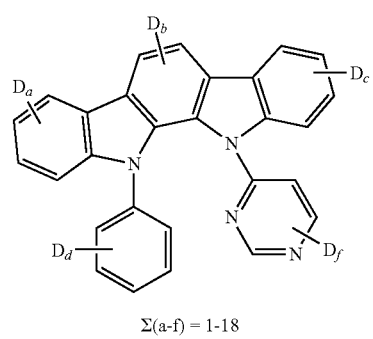
Σ(a-f) = 1-18
Compound H9
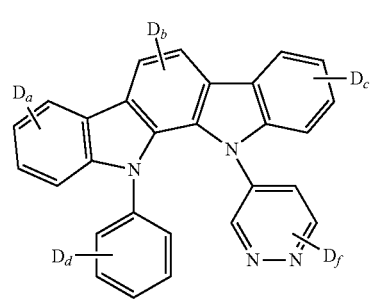
Σ(a-f) = 1-18
Compound H10
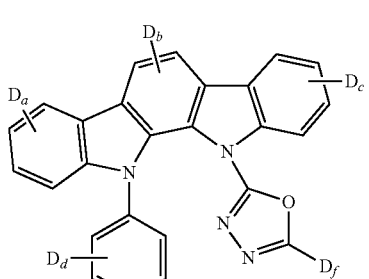
Σ(a-f) = 1-16

Compound H11
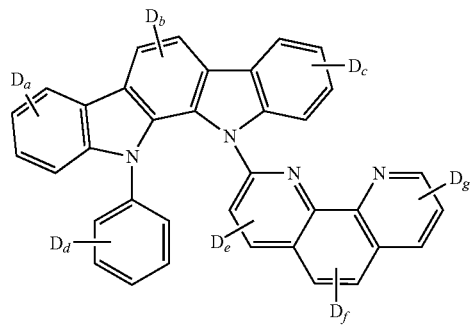
Σ(a-g) = 1-23
Compound H12
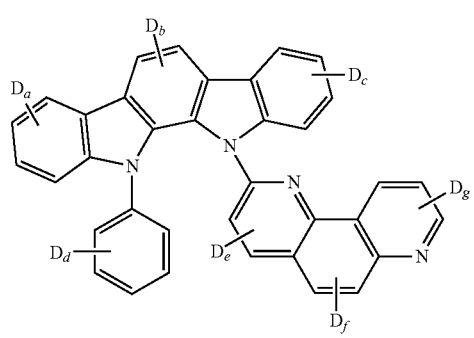
Σ(a-g) = 1-23
Compound H13
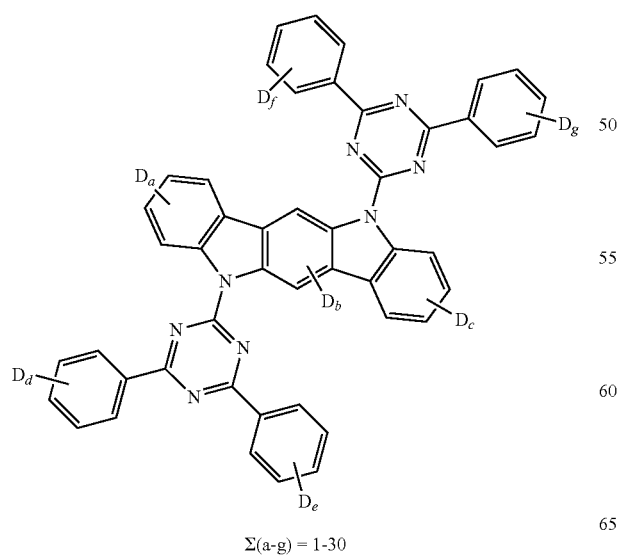
Σ(a-g) = 1-30
Compound H14
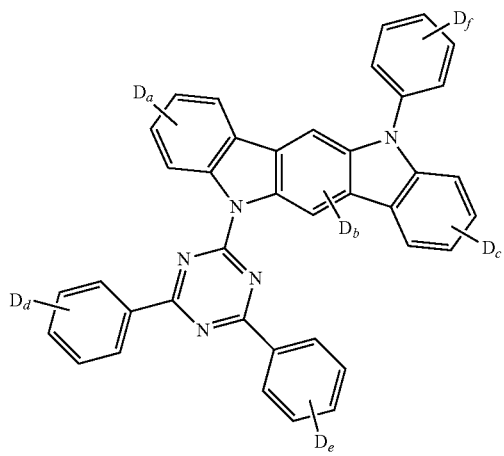
Σ(a-f) = 1-25
Compound H15
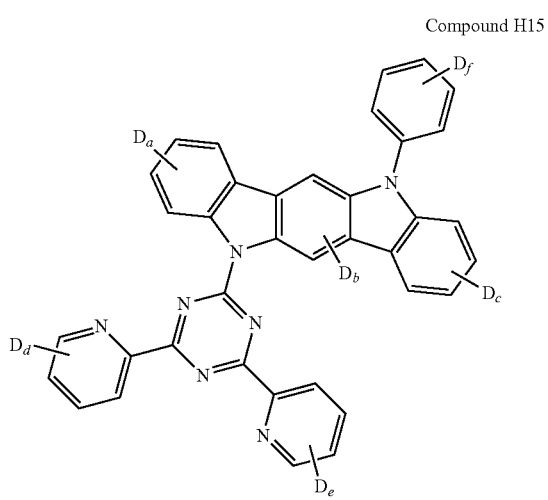
Σ(a-f) = 1-23
Compound H16
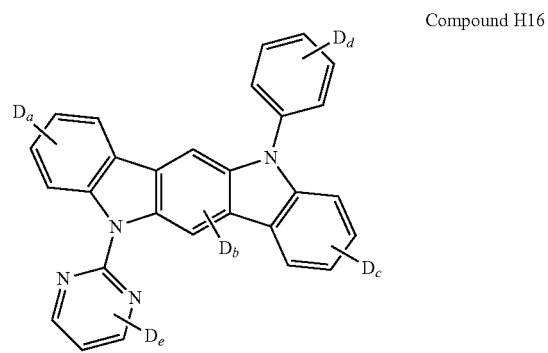
Σ(a-e) = 1-18

-continued

Compound H17

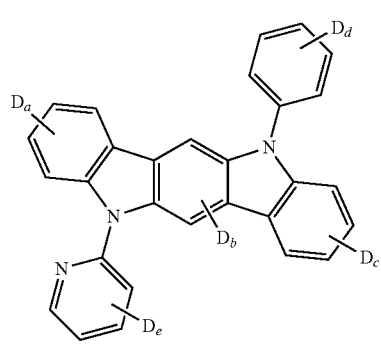

Σ(a-e) = 1-19

Compound H18

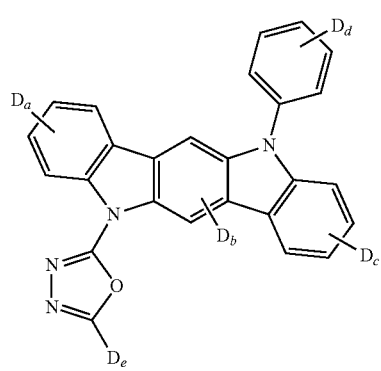

Σ(a-e) = 1-16

Compound H19

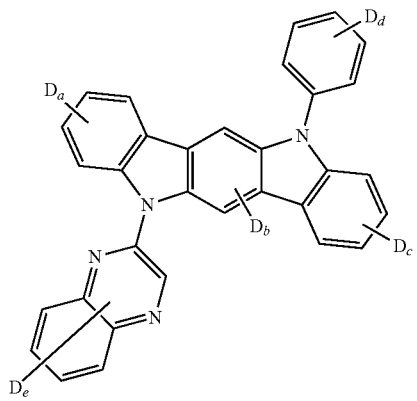

Σ(a-e) = 1-20

-continued

Compound H20

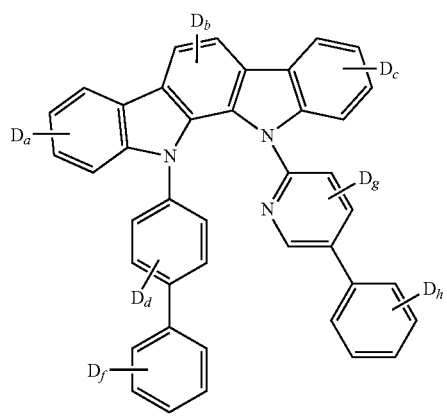

Σ(a-h) = 1-27

Compound H21

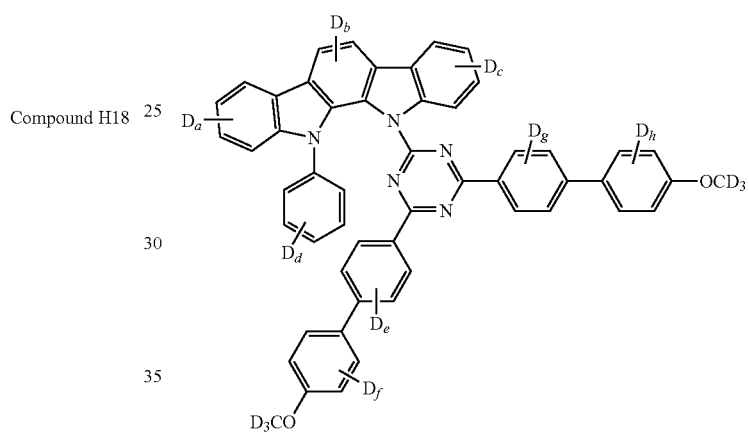

Σ(a-h) = 1-31

9. An organic electronic device comprising a first electrical contact layer, a second electrical contact layer, and at least one active layer therebetween, wherein the active layer comprises an indolocarbazole compound having at least one deuterium substituent.

10. The device of claim 9, wherein the indolocarbazole compound has Formula I or Formula II:

Formula I

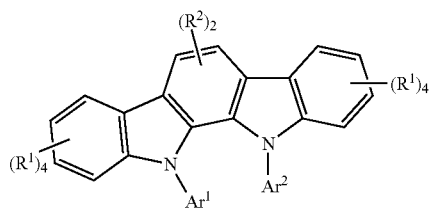

Formula II

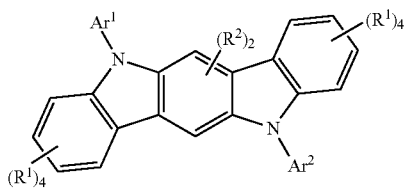

wherein:
- $Ar^1$ is an aromatic electron transporting group;
- $Ar^2$ is selected from the group consisting of aryl groups and aromatic electron transporting groups; and
- $R^1$ and $R^2$ are the same or different at each occurrence and are selected from the group consisting of H, D and aryl;

wherein the compound has at least one D.

11. The device of claim 9, wherein the active layer is an electroactive layer which further comprises an electroactive dopant capable of electroluminescence having an emission maximum between 380 and 750 nm.

12. The device of claim 10, wherein the active layer is an electroactive layer and consists essentially of a compound having Formula I or Formula II and an electroactive dopant compound.

13. The device of claim 11, wherein the electroactive dopant is a cyclometalated complex of iridium or platinum.

* * * * *